(12) United States Patent
D'Alessio et al.

(10) Patent No.: US 8,343,183 B2
(45) Date of Patent: Jan. 1, 2013

(54) SELF-CONTAINED MEDICAL APPLICATORS FOR SURGICAL SEALANTS, AND METHODS OF USE THEREOF

(75) Inventors: Keith R. D'Alessio, Cary, NC (US); Matthew Justin Morton, Holly Springs, NC (US); John L. Manhard, Durham, NC (US); Stephen William Cline, Morrisville, NC (US); Jared Daniel Goodnow Butlin, Durham, NC (US); John Conn, San Diego, CA (US)

(73) Assignee: HyperBranch Medical Technology, Inc., Durham, NC (US)

( * ) Notice: Subject to any disclaimer, the term of this patent is extended or adjusted under 35 U.S.C. 154(b) by 449 days.

(21) Appl. No.: 12/771,656

(22) Filed: Apr. 30, 2010

(65) Prior Publication Data
US 2010/0280312 A1 Nov. 4, 2010

Related U.S. Application Data

(60) Provisional application No. 61/174,153, filed on Apr. 30, 2009.

(51) Int. Cl.
*A61B 17/08* (2006.01)
*A61D 1/00* (2006.01)
(52) U.S. Cl. ...................................................... 606/214
(58) Field of Classification Search ................... 606/214
See application file for complete search history.

(56) References Cited

U.S. PATENT DOCUMENTS

| | | | |
|---|---|---|---|
| 4,735,616 A | 4/1988 | Eibl et al. | |
| 4,874,368 A | 10/1989 | Miller et al. | |
| 5,080,649 A | 1/1992 | Vetter | |
| 5,368,563 A | 11/1994 | Lonneman et al. | |
| 5,474,540 A | 12/1995 | Miller et al. | |
| 5,860,739 A | 1/1999 | Cannon | |
| 5,971,953 A | 10/1999 | Bachynsky | |
| 6,648,852 B2 | 11/2003 | Wirt et al. | |
| 2002/0035351 A1 | 3/2002 | Lodice | |
| 2008/0195040 A1 | 8/2008 | Clark et al. | |
| 2010/0010473 A1* | 1/2010 | D'Alessio et al. | 604/520 |

OTHER PUBLICATIONS

International Search Report and Written Opinion of the ISA from PCT/US2010/033183 dated Jan. 3, 2010.

(Continued)

*Primary Examiner* — Melanie Tyson
(74) *Attorney, Agent, or Firm* — Dana M. Gordon; Foley Hoag LLP

(57) ABSTRACT

Aspects of the invention relate to an applicator, and methods of use thereof, which can house multiple component formulations in separate material receptacles, which components can then be easily combined at the time of use without assembly by the user. In certain embodiments, a device of the invention can be used for, but is not limited to, applying hydrogel formulations to dura mater, abdominal tissue in hernia repair, tissues near the spine, lung tissue, intestinal tissue, or any of the internal tissues. In certain embodiments, a device of the invention can be configured to apply a spray or a stream of a liquid formulation to a surface. In certain embodiments, a device of the invention can be configured to deliver the formulation through an endoscope or laparoscope.

20 Claims, 11 Drawing Sheets

OTHER PUBLICATIONS

Chen, C.Z., et al.; "Incorporation of dimethyldodecylammonium chloride functionalities onto poly(propylene imine) dendrimers significantly enhances their antibacterial properties." *Chem Commun.* 1585-1586 (1999).

Elliott, G.F., et al.; "Cornea, and the swelling of polyelectrolyte gels of biological interest." *Rep. Prog. Phys.* 61:1325-1365 (1998).

Haldar, J., et al.; "Polymeric coatings that inactivate both influenza virus and pathogenic bacteria." *Proc. Natl. Acad. Sci. USA* 103(47):17667-17671 (2006).

Lin, J., et al.; "Bactericidal properties of flat surfaces and nanoparticles derivatized with alkylated polyethylenimines." *Biotechnol Progress* 18:1082-1086 (2002).

Lin, J., et al.; "Making thin polymeric materials including fabrics microbicidal and also water-repellent." *Biotechnology Letters* 25(19):1661-1665 (2003).

Lin, J., et al.; "Mechanism of Bactericidal and Fungicidal Activities of Textiles Covalently Modified With Alkylated Polyethylenimine." *Biotechnol Bioeng.* 83:168-172 (2003).

Milovic, N. M., et al.; "Immobilized N-alkylated polyethylenimine avidly kills bacteria by rupturing cell membranes with no resistance developed." *Biotechnol Bioeng.* 90:715-722 (2005).

Suh, J., et al.; "Ionization of poly(ethylenimine) and poly(allylamine) at various pHs." *Bioorg. Chem.* 22:318-327 (1994).

* cited by examiner

SIDE VIEW

[A]

TOP VIEW

[B]

Flattened End of Fitment

[A]

[B]

SIDE VIEW

[A]    21

TOP VIEW

[B]

SELF-CONTAINED MEDICAL APPLICATORS FOR SURGICAL SEALANTS, AND METHODS OF USE THEREOF

RELATED APPLICATION

This application claims the benefit of priority to U.S. Provisional Patent Application Ser. No. 61/174,153, filed Apr. 30, 2009; the contents of which are hereby incorporated by reference.

BACKGROUND

A number of medically useful compositions comprise two or more ingredients that for optimal results should not be mixed together until shortly prior to use. In some instances, at least one of the ingredients is a solid, often a powder, while at least one of the other ingredients is a liquid in which the solid ingredient is to be dissolved. Therefore, it is desirable to have an applicator that can easily deliver multiple-component formulations for use in the body, which applicators are capable of keeping the individual components separated during storage and mixing them prior to application.

Use of a dual-ingredient composition can be accomplished with a conventional syringe by first loading one ingredient into the syringe, then adding the second ingredient, shaking the syringe or otherwise agitating the contents to achieve mixing, and subsequently dispensing the resulting mixture in the usual manner. This procedure, however, presents substantial shortcomings, including contamination and loss of sterility. For example, using a conventional syringe of the kind that is filled through a fill needle connected to the outlet orifice of the syringe, it is necessary to replace the needle after the first ingredient has been drawn into the syringe in order to avoid contamination of the supply of the second ingredient. Even then it may be difficult to complete the procedure without rendering the outlet portion of the syringe non-sterile, e.g., by extended contact with air. Another technique that may be employed utilizes a syringe of generally conventional construction in which one ingredient has initially been loaded into the syringe, usually followed by a sterilization procedure. Again, however, it is often rather difficult to load the syringe with the second ingredient without undermining the sterile characteristics of the syringe. Moreover, in both of these procedures the user's manipulative steps are complex enough that some difficulty may be experienced.

One approach to this problem is described in U.S. Pat. No. 5,080,649, incorporated by reference herein in its entirety. Therein is described a hypodermic syringe which has an elongated tubular body having a front end adapted to carry a needle, a rear end, and a bypass between the ends, wherein a front partition piston defines with the front end a front compartment adapted to hold a substance and a rear piston defines with the front piston a rear compartment adapted to hold a fluid miscible with the front-compartment substance; and the front piston is displaceable into a middle position in the bypass for fluid communication between the compartments.

Some medical sealants are examples of medically useful compositions which comprise two or more ingredients that are not mixed together until shortly prior to use. Medical sealants and adhesives play an important role in helping patients recover from surgery or trauma. In particular, sealants and adhesives are useful in treating patients suffering from a variety of internal or topical conditions, including lacerations, tears, wounds, ulcers, anastomoses, and surgical procedures. Sealants or adhesives can generally be used in any indication or application for which a suture or staple is presently used, and the sealant or adhesive often provides a better outcome than a suture or staple. Sealants or adhesives can also be applied more quickly to the injury site and often provide a better seal over the wound, and ultimately improved healing, in comparison to a conventional suture or staple.

There are at least two medical sealant/adhesive products, CoSeal and DuraSeal, currently on the market which are based on hydrogel formulations. Both products comprise multiple components housed in separate containers. CoSeal Surgical Sealant (CoSeal) is composed of two synthetic polyethylene glycols (PEGs), a dilute hydrogen chloride solution and a sodium phosphate/sodium carbonate solution. The DuraSeal Dural Sealant System consists of components for preparation of a synthetic, absorbable sealant and an applicator for delivery of the sealant to the target site the sealant is composed of two solutions, a polyethylene glycol (PEG) ester solution and a trilysine amine solution. However, the products have shortcomings because the devices need to be assembled at the time of use and they utilize static mixing systems that allow the hydrogel formulation to gel within the mixing nozzle, precluding a start-and-stop application technique.

Fibrin glues are also sold in packaging and applicator systems that are similar to those used for CoSeal and DuraSeal. One example is Baxter's Tisseel. Tisseel VH [Fibrin Sealant] consists of a two-component fibrin biomatrix that offers highly concentrated human fibrinogen to seal tissue and stop diffuse bleeding.

Baxter also offers different types of applicators, for example, Duploject; Easyspray; and DuploSpray MIS. Duploject is a reconstitution device that offers needle free easy preparation. Easyspray is a disposable set consisting of a dual-lumen connector hose, a sterile filter, two spray heads and a clip to be attached to the Duploject plunger for gas activation. DuploSpray MIS applicator is a disposable spray applicator consisting of a stainless steel shaft, dual lumen spray tubing, sterile filter and two replaceable spray tips.

Further, Micromedics, Inc., a medical device manufacturer in St. Paul, Minn., manufactures an endoscopic spray system for biomaterials called the FibriJet®. FibriJet® incorporates a gas-assisted spray system. Spraying of fibrin glues are also discussed in the patent literature; see: U.S. Pat. Nos. 5,474,540; 4,874,368; and 5,368,563; all of which are hereby incorporated by reference. See also U.S. Pat. No. 4,735,616, hereby incorporated by reference, which describes a twin bypass syringe for the delivery of fibrin glue products.

SUMMARY

Certain aspects of the invention relate to an applicator which can house multiple component formulations in separate material receptacles, which can then be easily reconstituted at time of use with little or no assembly by the user. A further objective of the invention is to provide an applicator system for which the manipulative steps required for use are minimized and/or the number of device components is held to a minimum.

In certain embodiments, a device of the invention can be used for, but is not limited to, applying hydrogel formulations to dura mater, abdominal tissue in hernia repair, tissues near the spine, lung tissue, intestinal tissue, or any of the internal tissues. In certain embodiments, a device of the invention can be configured to apply a spray or a stream of liquid formulation onto a surface to be treated. In certain embodiments, a device of the invention can be configured to deliver the formulation through a trocar in a scope (e.g., an endoscope or laparoscope).

One aspect of the invention relates to an applicator system, and methods of use thereof, that can be used to house separately liquids, viscous liquids and solids (e.g., components of a polymerizable hydrogel), is further designed to facilitate the dissolution of the solids inside the applicator, and is also designed to facilitate the application of the mixture to a surface. In certain embodiments, such an applicator may be used for delivering a composition to a tissue. For example, such an applicator may be used for delivering a formulation to the dura or a cornea. In addition, the applicators may be useful for a variety of other applications, including, for example, preparation and application of a vascular sealant or arterial access closures.

In certain embodiments, the applicator contains at least two sealed chambers: a first chamber containing a solid, a viscous liquid or a liquid; and a second chamber containing a liquid. For example, when a user wishes to use the applicator, he or she causes a floating plunger to advance through a syringe barrel opening a fluid bypass from the chamber containing the liquid into the chamber containing the solid, viscous liquid or liquid. The liquid then flows through the bypass into the chamber containing the solid, viscous liquid or liquid, where the liquid comes into contact with the solid, viscous liquid or liquid. The applicator can then be optionally agitated to promote thorough mixing of the materials. Continued motion of the plunger and syringe housing, results in the expulsion of the solid/liquid mixture into a nozzle assembly, and then onto or into a patient. In certain embodiments, a motor and gear train are used to effectuate the piercing of the solid-containing chamber and the movement of the plunger and/or housing.

In certain embodiments, the present invention describes how the functionality of a spray applicator can be extended beyond what is normally possible for a spray applicator system. In one embodiment, a tubular fitment is added to the distal end of the air-assisted spray applicator to limit the width of spray application. In a second embodiment, the fitment allows for a surgeon to apply a hydrogel formulation across a gap of loosely approximated tissue surfaces. In a third embodiment, the fitment consists of a spatula-like piece which is placed under the incision line and allows for the formulation to be sprayed over a gap and yet still form a integrated leak-free application of formulation to loosely approximated tissues such as dura mater.

DETAILED DESCRIPTION

Figure 1:
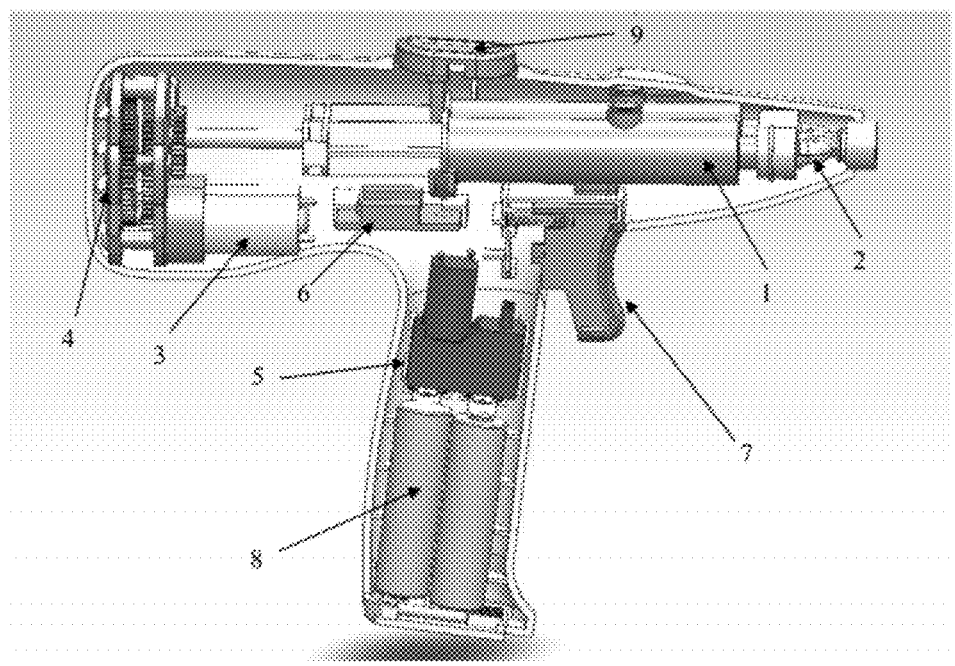
FIG. 1 depicts one embodiment of a battery-powered device.

There is a need to develop improved medical dispensers that facilitate the complete mixing of solids and/or liquids inside the dispenser while maintaining the sterility of the mixture. In addition, there is a need for medical dispensers that allow two or more components which are to be mixed to be kept separate until just prior to use. Further, it would be advantageous if the dispensers could also act as applicators, thereby facilitating the application of the mixture. The present invention addresses these needs and others.

One aspect of the invention relates to an applicator system that may be used to house multiple components (e.g., components of a polymerizable hydrogel, such as solids and liquids), facilitating the mixing of the components inside the applicator, and further facilitating the application of the mixture. Another aspect of the invention relates to an applicator system that may be used to house multiple liquids and a solid (e.g., components of a polymerizable hydrogel), facilitating the mixing of the solid and liquids inside the applicator, and further facilitating the application of the mixture. Another aspect of the invention relates to an applicator system that may be used to house two liquids and two solids (e.g., components of a polymerizable hydrogel), facilitating the mixing of the solid and liquid inside the applicator, and further facilitating the application of the mixture. Another aspect of the invention relates to an applicator system that may be used to house two liquids and one solid (e.g., components of a polymerizable hydrogel), facilitating the mixing of the solid and liquid inside the applicator, and further facilitating the application of the mixture.

While the invention will often be described herein as facilitating the formation and effective delivery to a patient of a polymerizable hydrogel formulation, this characterization is not intended in any way to limit the scope of the invention to such an application. Rather, the applicators of the invention, and the methods of the invention, may be used in any application requiring mixing two or more components (e.g., solids and liquids) prior to use. It is understood that these applicators may be useful for a variety of applications including, for example, treating/sealing/adhering dura mater, cardiovascular tissue, ducts, bladders, lung tissue, liver, other parenchymal organs, as well as adhering soft tissue mesh to the body.

In certain embodiments, the applicators of the invention can be used to prepare and apply a hydrogel formulation. In certain embodiments, the hydrogel formulation is delivered in liquid form and quickly polymerizes into a hydrogel. In certain embodiments, the hydrogel formulation comprises a cross linker (such as PEI); an activated polymer (such as activated PEG); and a buffer solution or solutions.

One aspect of the invention relates to a device which incorporates several separate receptacles for containing various formulation components. The various components are separate and remain stable during their intended shelf life. These receptacles are segregated into groups by various functions especially when used in reactive chemistry systems as described herein. In certain embodiments, these multiple separate receptacles can be grouped from the back of the applicator towards the front of the applicator in terms of which materials must be mixed first in order to prepare correctly the formulation for ultimate delivery. The most proximal receptacle(s) are then engaged by a power source and move towards the front (distal) end of the applicator. A lock mechanism prevents the opening of the receptacle which, after the opening of a bypass, contains two components (e.g., a solid and a liquid).

Once the mixing is complete, the lock mechanism can be disengaged and the system can be re-energized to engage more distal receptacles. This serial engagement of a power source, engagement of a more distal receptacle and expulsion of the material in the more proximal receptacle can occur in a series of steps until the desired formulation is prepared or "reconstituted."

In other embodiments, similar groups of receptacles can be added in parallel to build a reactive system which is "reconstituted" in the first set of power engagements, but is not fully mixed for final reaction until the last engagement of the power source at the most distal end of the applicator, whereupon the mixed formulation exits the applicator. Therefore, the possible configurations become a two-dimensional matrix of possible receptacle configurations. Starting with a one-part formulation with more than one constituent (for example, 2, 3, 4 or more constituents), and progressing to a two-part formulation with two groups of receptacles and each group with more than one constituent, to a three part formulation with three groups of receptacles, etc. The system is completely scalable in both dimensions with respect to the number of constituents in a particular part and for the number of parts in the overall formulation (or groups of receptacles). For example, one aspect of the invention relates to an applicator which comprises a set of two bypassing syringes mated with a spray applicator tip.

As used herein, the term "reconstitution" means the mixing of more than one component into a formulation or formulation part which is at least meta-stable for some amount of time. It also includes dissolution (i.e., the process in which one substance is dissolved in another.) In certain embodiments, the individual components may not be stable in the "reconstituted" state or may suffer from other difficulties such as tolerance to sterilization procedures which makes it necessary for the components to be separate during the bulk of the storage time of the device but allow for it to be "reconstituted" into a formulation or formulation part prior to application.

In addition, while certain aspects of the invention have been described above as containing a series of receptacles for constituents which mix starting at the proximal end and working towards the distal end of the applicator, and exit through the most distal end of the applicator, alternative arrangements of components are also envisioned. In particular, those skilled in the art will understand that it would be possible to build applicators such that mixing begins at the distal end of the device and progresses toward the proximal end. In one example of such an applicator, a fluid pathway would be constructed to convey the formulation or formulation parts back towards the distal end of the device for discharge onto the surface being treated.

In certain embodiments, the arrangement of constituent receptacles is housed within an applicator body. This body can have any of several form factors. For example, the applicator can be shaped like a gun with a pistol style grip, a pen, or any number of other form factors.

Figure 4:
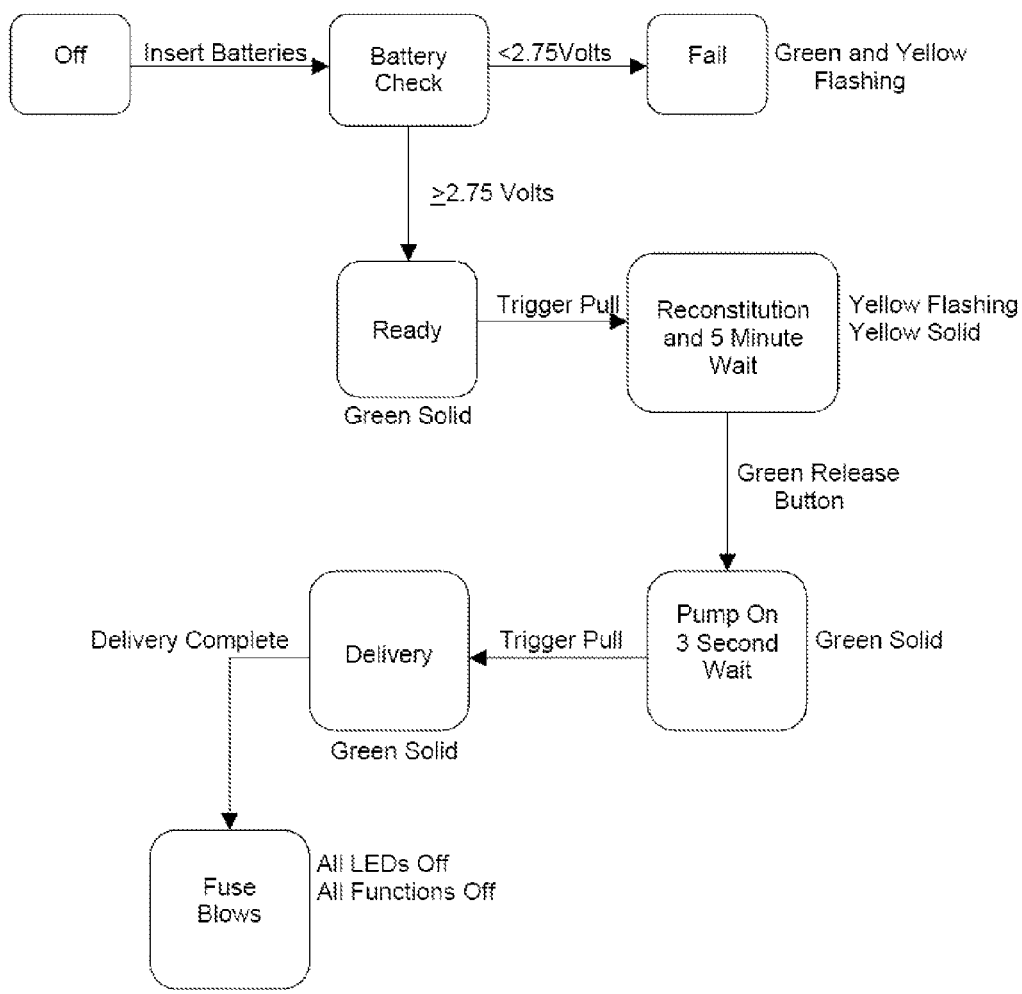
FIG. 4 is an example of an Operational Flow Chart for an electronic device.

In certain embodiments, a programmable logic controller (PLC) and electronic control measures may be used to add additional functionality and robustness to the device. However, it is understood by those skilled in the art that similar functionality could be accomplished through mere mechanical controls or by any combination of mechanical and electric controls without the use of a PLC or other sophisticated electronics. Those of ordinary skill in the art will recognize that the use of a PLC allows for efficient modification of the system's functionality via adjustment of the software logic steps. Certain embodiments utilize the logic steps shown in the FIG. 4 to impart warning and device status information to the user.

In certain embodiments, a hybrid sterilization system is utilized, using radiation to sterilize the chemical components and ethylene oxide to sterilize the mechanical components. For example, in certain embodiments a sealed, filled mixing chamber with two active ingredients and two buffer solutions is first sterilized via radiation, and then assembled into an applicator, which is then sterilized with ethylene oxide or hydrogen peroxide.

In certain embodiments, an air atomization nozzle is used. However, the air atomization nozzle assembly could be replaced by another type of atomizer (such as a piezoelectric atomizer, which would not require compressed air). In addition, in certain embodiments, a piezoelectric or electric motor vibrator (similar to a cell phone vibrator) could be used via a PLC logic control step to facilitate dissolution during reconstitution.

In certain embodiments, air is supplied via a battery powered air pump.

Importantly, the devices described herein are scalable to formulation configurations requiring additional formulation components. For example, if it were desirable to deliver a three-part formulation, each part consisting of a reconstitution liquid and an active agent, the current device could be scaled up to include three cylindrical chambers with bypasses. Likewise, devices are scalable in the other direction in that two formulation parts of three separate constituents each, could be easily designed with separate cylindrical chambers for each formulation part, each cylindrical chamber in this case incorporating two floating plungers, two bypasses and a driven plunger. Thus devices are scalable in both directions for as many formulation parts and individual formulation part components as required.

In certain embodiments, drug(s) and/or medicament(s) could be added as a formulation part or formulation part component(s).

Further, there are many different power sources which can be used to effect the reconstitution and expulsion of the mixed formulation. These include, for example, compressed gas, mechanical power (such as compressed springs), electrical power, and chemical power (such as acid and $NaHCO_3$). In certain embodiments, the chosen power source is a battery. In certain embodiments, the chosen power source can be engaged by use of a trigger, a button or other means.

In certain embodiments, the final output of the device can either deliver a stream of mixed formulation or a spray of mixed formulation.

In certain embodiments, devices of the invention can be fitted with a mixing nozzle such that it could deliver a stream of mixed formulation to a particular area. It is also contemplated that the nozzle be adapted to pass through an endoscope or laparoscope (thereby allowing use in minimally invasive surgery).

In certain embodiments, one can optimize spray capability and reduce the delivery rate of adhesive, e.g., by changing the orifice size and pressure regulation of the drive train and atomization pathways. In addition, by changing the orifice shape, one can optimize spray patterns.

In certain embodiments, fitments may be added to the tip of a spray applicator in order to give the applicator additional functionality above that possible with a traditional spray application system. As used herein, a "fitment" refers to an accessory attached to the dispensing end of an applicator (i.e., the outlet).

For some applications, there is a need to limit the spray pattern to a more narrow range than initially possible for a conventional air-assisted spray applicator. For example, a Micromedics spray applicator will spray a swath approximately 2.5 inches in width when held 2.75 inches from the surface of the area to be sprayed. Remarkably, when a simple tube (a type of fitment) is attached to the front of the Micromedics air assisted applicator, a change in the spray pattern is realized. In addition, it is disclosed herein that the length of the tube has a large effect on the spray pattern. In certain experiments, a tube of approximately 0.3 inches in length reduced the spray pattern to 0.9 inches wide, whereas a tube of approximately 0.6 inches in length resulted in the spray coalescing within the tube and thus expelling out of the tube in the form of a discontinuous stream (when held 2.75 inches from the surface of the area to be sprayed). Thus, by careful selection of tube length a reduced-width spray pattern may be accomplished. A reduced-width spray pattern is desirable in several applications in order to avoid or limit the spraying of unintentional areas. For example, in the spray application for dural repair, the inadvertent application of formulation to the exposed cranium is highly undesirable. In certain embodiment, the fitment may be easily attached and detached from the air-assisted spray applicator such that the device is easily configured for a broad spray (without fitment) or a reduced width spray pattern with fitment, as needed by the physician user.

Figure 3A:
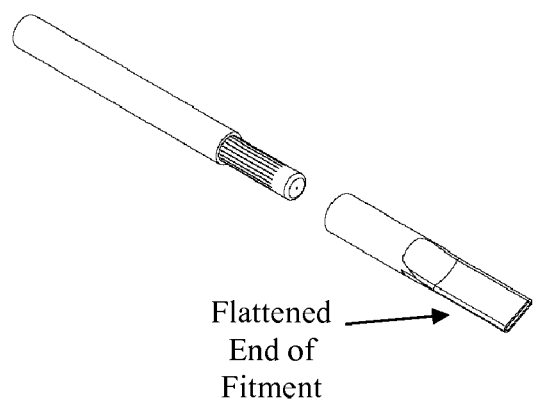
FIG. 3A depicts a fitment with a flattened end.
Figure 3A:
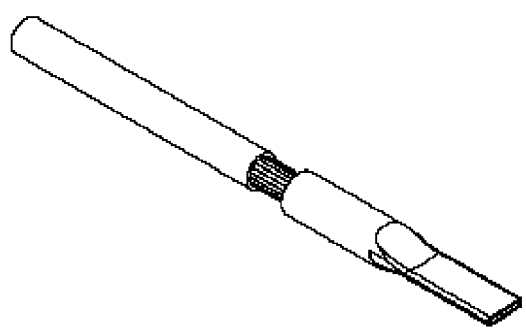
Figure 3A:

In addition, there may be times in which a user (e.g., a physician) may find it more desirable to deliver the formulation in the form of a stream rather than a spray. The concept of offering an easily detachable fitment can be used to meet this need. One example is the closure of the dura immediately after brain surgery. In many cases, the dura has been cut and reflected back in order to allow the surgeon access to the brain for, e.g., the removal of a tumor. During the time of the brain surgery, while the dura has been cut and reflected back, the dura itself often shrinks such that when closed, the opposite edges of dura no longer are in close approximation and many times have a gap up to 4 mm or so. In these cases, a spray application of formulation can not close the gap. By placing a tubular fitment with a flattened distal aspect onto an air-assisted applicator, a stream of gelling formulation can then be applied to the surface such that the gel overlays the gap and the edges of dural tissue and a water tight seal may be achieved. See FIG. 3A. This result cannot be obtained with a traditional spray applicator.

Figure 3B:
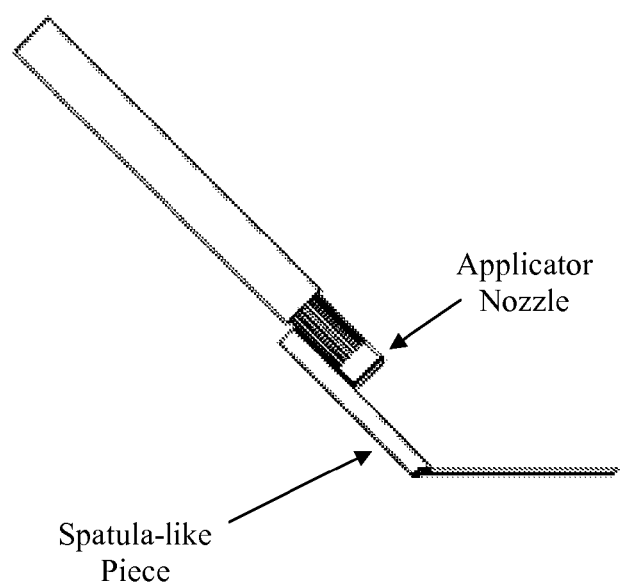
FIG. 3B depicts a fitment with a spatula-like piece.
Figure 3B:
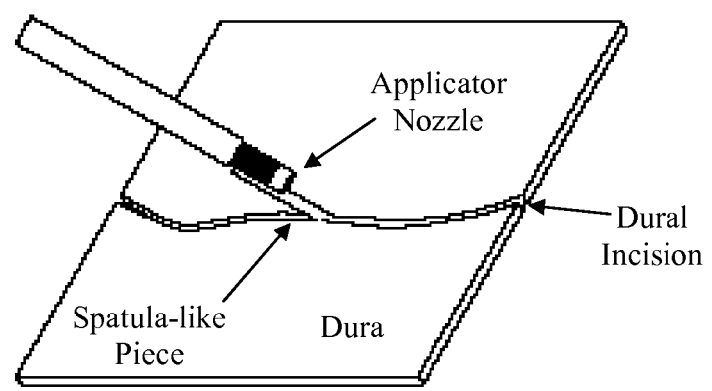

In other embodiments, the spray applicator has a spatula-like attachment which protrudes from the distal tip of the spray applicator. In use, the spatula-like attachment is placed under the dura such that when the spray applicator is engaged, the sprayed formulation strikes the dural tissue and the spatula-like attachment under the gap within the loosely approximated dura. See FIG. 3B. As the formulation gels, the spray applicator can be advanced and the gel will dislodge from the spatula surface and remain attached to the opposing sides of the dural incision. This process can be repeated as necessary, advancing along the dural incision until the entire incision is closed.

Figure 5:
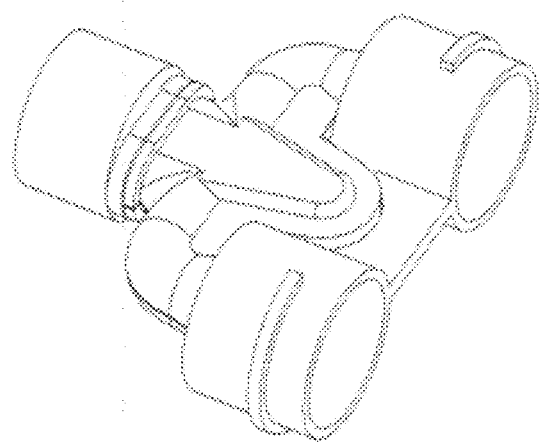
FIG. 5 depicts two views of an embodiment of a nozzle.
Figure 5:
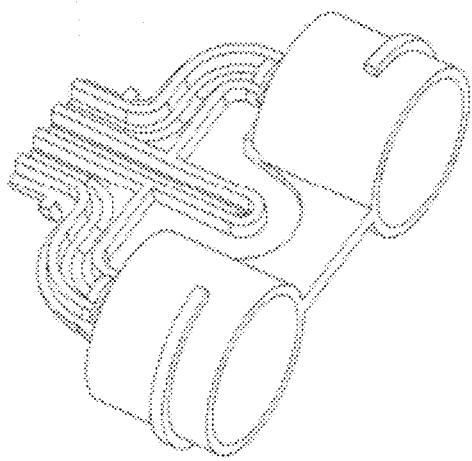
Figure 6:
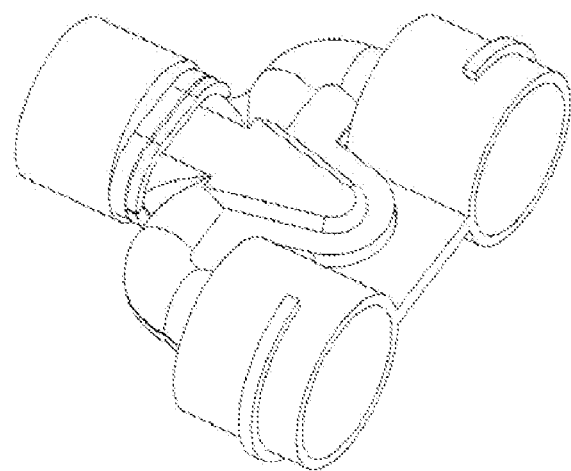
FIG. 6 depicts two views of an embodiment of a "staggered" nozzle.
Figure 6:
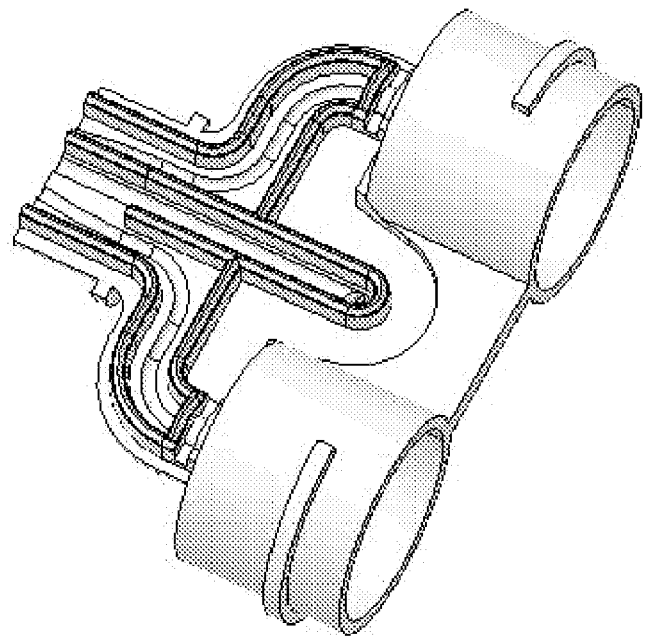

In addition, a variety of nozzle designs are disclosed herein (see, for example, FIGS. 5 and 6). In FIG. 5 is shown a nozzle wherein two liquid channels and one gas (e.g., air) channel meet near the end of the nozzle outlet. While such a nozzle assembly worked well, in some instances (such as when a device containing the nozzle was set down for several minutes) the nozzle could clog. FIG. 6 shows a design wherein one liquid channel and the gas channel combine, and then combine with the second liquid channel; such an approach substantially prevented occlusion within the nozzle.

In certain embodiments, the attachments described above may be used in combination to achieve results reflecting a combination of the results obtained with them separately.

Polyalkyleneimine Hydrogels

One aspect of the present invention relates to applicators for polyalkyleneimine hydrogels, and methods for using such applicators. Polyalkyleneimine hydrogels can be prepared by reacting a polyalkyleneimine (PAI) with a cross-linking agent, such as an activated polyethylene glycol. Polyalkyleneimine hydrogels are amendable to a variety of clinical treatments, such as incisions created during general surgery or wounds/incisions in the dura created during neurosurgery. Polyalkyleneimine hydrogels offer the advantage that the secondary and tertiary amino groups of the gel can be converted to secondary and tertiary ammonium cations which may encourage cell attachment and cell ingrowth. In certain instances, the secondary and tertiary amines of the polyethyleneimine (PEI) can be converted to ammonium cations by placing the PEI in an aqueous solution.

Polyalkyleneimine (PAI) hydrogels are known to have superior adhesion properties. Their superior tissue-adhesion properties may be due to two factors. First, the cationic properties of PEI promote interaction with, and possibly penetration within, an anionic tissue substrate. See *Rep. Prog. Phys.* 1998, 61, 1325-1365. Cationic interactions could occur through the secondary and tertiary ammonium cations of the PEI backbone or through primary amino groups that did not react with the cross-linking reagent. Second, PEI contains a large number of functional groups per molecule, thus promoting an increased number of crosslinkable sites within the polymer network. The increased number of crosslinkable sites within the polymer network affords dense, interpenetrating networks between the hydrogel and the tissue surface. The number of free amino groups in the hydrogel can be controlled by varying the ratio of PEI to activated PEG. The ability to control the number of free amino groups is significant because greater cell ingrowth was observed in tissue ingrowth experiments using hydrogels that contained a larger percentage of PEI.

In addition to increased adhesion, it has been found that as the molecular weight of the PEI increases from about 1,300 to about 2,000 g/mol the swelling of the resulting hydrogel decreases in certain instances. Thus, the molecular weight of the PEI may be adjusted in order to tune the swelling-effects of the resultant hydrogel.

A large variety of PAI derivatives are amenable to the present invention. For example, the amino groups of the PAI may be functionalized with a fatty acid, lower alkyl, an alkenyl, or alkynyl group. In addition, the amino groups or a portion of the amino groups may be functionalized to contain active agents, pharmaceutical agents, preservatives, radioisotopic ions, magnetically detectable ions, antibodies, medical contrast agents, colorants, dyes, or other visualization agents. In certain instances, about 1% to about 70% of the primary amines of the PEI are functionalized. The PAI derivatives may contain hydrolytically and/or enzymatically degradable linkages capable of releasing the functional derivatives, active agents, pharmaceutical agents, preservatives, radioisotopic ions, magnetically detectable ions, antibodies, colorants, dyes, or other visualization agents. Alternatively, a different nucleophile can be added to the PEI, such as a cysteine, isocysteine, thiol, or other such nucleophilic group. For example, a PEI can be modified such that all the primary amines are modified with a cysteine, thus affording a PEI derivative which can form crosslinked gel/networks using the amine, thiol, or both the amine and thio. In certain instances, an ureido, urea, acetoacetoxy, RGD peptide, EDTA, or carbohydrate group may be bonded to one or more of the amino groups of the PEI. Representative carbohydrates include erythrose, threose, ribose, arabinose, xylose, lyxose, allose, altrose, glucose, mannose, gulose, idose, galactose, talose, sucrose, lactose, and the like. It is possible that the ureido group and urea group will impart adhesion partially via a cation/anion interaction. The acetoacetoxy group may adhere to tissue by making a metal complex on the surface of the tissue.

In certain instances, the PEI is functionalized so that both primary amino ($-NH_2$) groups and thiol ($-SH$) groups could react with electrophilic groups or a combination of them, such as an acrylate, succinimidyl ester, maleimide, ester, or aldehyde. The electrophilic groups can be attached to poly(alkyleneoxide) (e.g., PEG, PPG or PEG-PPG) polymers. Two or more electrophilic groups are required. Of course, the degree of PEI functionalization may be varied in order to obtain the desired physical properties of the resultant gel. In certain instances, only about 1% of the primary amino groups of the PEI are functionalized. In other instances, about 5% to about 25% of the primary amino groups of the PEI are functionalized. In other instances, about 25% to about 50% of the primary amino groups of the PEI are functionalized. In other instances, about 99% of the primary amino groups of the PEI are functionalized. In certain instances, one or more of the amino groups are reacted with an epoxide or acylating agent. In certain instances, one or more of the amino groups are reacted with an isocyanate.

The molecular weight of the PEI may be adjusted to tune the physical properties of the gel formed by addition of the cross-linking agent. In certain instances, the PEI has a weight average molecular weight of about 400 g/mol to about 2,000,000 g/mol. In certain instances, the PEI has a weight average molecular weight of about 400 g/mol to about 1,000,000 g/mol. In certain instances, the PEI has a weight average molecular weight of about 400 g/mol to about 500,000 g/mol. In certain instances, the PEI has a weight average molecular weight of about 400 g/mol to about 100,000 g/mol. In certain instances, the PEI has a weight average molecular weight of about 400 g/mol to about 50,000 g/mol. In certain instances, the PEI has a weight average molecular weight of about 400 g/mol to about 10,000 g/mol. In certain instances, the PEI has a weight average molecular weight of about 400 g/mol to about 5,000 g/mol. In certain instances, the PEI has a weight average molecular weight of about 400 g/mol to about 2,000 g/mol.

In certain instances, the polyalkyleneimine has a weight average molecular weight of about 600 to about 10,000 Daltons, the polyalkylene glycol has a weight average molecular weight of about 500 to about 20,000 Daltons, and the molar ratio of the polyalkyleneimine to the polyalkylene glycol is within a molar range of about 0.025:1 to about 0.4:1. In certain instances, the hydrogel reaches equilibrium swelling in about 5 to about 30 hours. In certain instances, the hydrogel reaches equilibrium swelling in about 18 hours.

In certain instances, the aforementioned polyalkyleneimine/polyalkylene glycol hydrogels may be used or modified to non-covalently carry or contain active agents, pharmaceutical agents, preservatives, radioisotopic ions, magnetically detectable ions, antibodies, medical contrast agents, colorants, dyes, or other visualization agents.

Many prior sealant systems are not optimal because the sealant system may degrade before appreciable healing or tissue ingrowth occurs. For example, tissue ingrowth often begins within one week after application of the sealant, and complete tissue ingrowth may occur within 28 days after application of the sealant in very porous systems. However, many prior sealant systems contain degradable linkages which can cause the hydrogels to degrade before appreciable tissue ingrowth occurs. While use of these materials alone is not advantageous, these materials may be used as masking materials. Accordingly, in certain instances, when polyalkyleneimine hydrogel are used as covering materials the covering can maintain its mechanical strength for at least about 7 days. In certain instances, the polyalkyleneimine hydrogel sealants of the invention maintain mechanical strength for at least about 20 days. This rate of degradation allows the masking material to degrade, while keeping the covering material in place.

Since charged species encourage tissue growth, polyalkyleneimines are advantageous as masking material because they allow for incorporation of a large number of charged species. The charged species are created by converting unreacted primary amines, and internal secondary and tertiary amines into ammonium cations under physiological conditions. Table 1 below illustrates the number of primary, secondary and tertiary amines contained in various crosslinkers based on a polymer system having eighteen primary amines. As illustrated in Table 1, the trilysine crosslinker contains only primary amines and a pendant carboxylate while a PPI (DAB)-G1 dendrimer adds 9 units of potential cationic charge with the addition of 9 tertiary amines. The $PEI_{800}$ adds 14 units of potentially charged species (i.e., 155% more charge) compared to the PPI(DAB)-G1 dendrimer, while the $PEI_{2000}$ adds 26% more potentially charged species than $PEI_{800}$. Finally, $PEI_{25000}$ adds 24% more potentially charged species than $PEI_{2000}$, owing to the increased number of secondary and tertiary amines. Since the number of secondary and tertiary amino groups increases with increasing molecular weight of the polyalkyleneimine, the polyalkyleneimine hydrogels of the invention can be tuned by incorporating crosslinkers with varying molecular weights, and hence charge density, in order to affect the tissue ingrowth and degradation properties of the hydrogel.

TABLE 1

| Crosslinker | 1° amines | 2° amines | 3° amines |
|---|---|---|---|
| $PEI_{25000}$ | 18 | 22 | 14 |
| $PEI_{2000}$ | 18 | 17 | 12 |
| $PEI_{800}$ | 18 | 14 | 9 |
| PPI(DAB)-G1 | 18 | 0 | 9 |
| Trilysine | 4 | 0 | 0 |

Again, when used as masking material, polyalkyleneimine hydrogel sealants offer an advantage over prior sealant systems because polyalkyleneimines, especially derivatized polyalkyleneimines, should have antimicrobial and antiviral activity. Recent reports indicate that both polyalkyleneimines and derivatives thereof have antimicrobial properties, while lacking activity against mammalian cells. See *Biotechnol. Bioeng.* 2005, 90, 715-722; *Biotechnol. Bioeng.* 2003, 83, 168-172; *Biotechnology Letters* 2003, 25, 1661-1665; *Biotechnol. Prog.* 2002, 18, 1082-1086; *Chem. Commun.* 1999, 1585-1586; and *Proc. Nat. Acad. Sci. USA* 2006, 103, 17667-17671. Thus, hydrogels prepared from polyalkyleneimines may help fight, inhibit, prevent or even eliminate the chance for infection when applied to the tissue of a patient. Since the presence of cationic groups, especially quaternary amines, may influence the antimicrobial properties of the hydrogel, the PAI, in certain instances, may be derivatized with one or more quaternary amines. In certain instances, the PAI may be derivatized with four or more quaternary amines. In certain instances, the PAI may be derivatized with ten or more quaternary amines. Since the presence of cationic groups and hydrophobic side chains, when combined, tend to confer better antimicrobial properties, the PAI, in certain instances, may be derivatized with one or more quaternary amines and one or more fatty acid, lower alkyl, alkenyl, or alkynyl groups.

Polyalkyleneimine hydrogels offer the additional advantage that the amino groups of the polyalkyleneimine can act as a buffering agent. The ability to control the pH during preparation of the hydrogel is important because certain pHs are optimal for crosslinking of the components. In particular, the pH of a mixture of crosslinking components can affect the rate at which the crosslinking reaction takes places. In some instances, the desired pH can be achieved by adding a buffering agent, such as phosphates, carbonates, borates, and the like, to the solution containing the crosslinking components. However, when using poly alkyleneimines as a crosslinkable component, the primary, secondary, and tertiary amines act as buffering agents to provide some buffering capacity throughout a wide range of pHs. See *Bioorganic Chemistry* 1994, 22, 318-327. Moreover, as the crosslinkable component reacts, some of the amines are removed from solution, thereby reducing the pH. Since quick set-times can require higher pHs, it is advantageous to use a crosslinkable component which influences the pH so that the pH will lower to more physiological levels soon after mixing. This buffering feature of polyalkyleneimines eliminates the need for a strong buffer to achieve the high pH-levels sometimes used in preparing a hydrogel. Notably, addition of strong buffers may not be desirable because such buffers may remain in the sealant and cause the patient's tissue to become irritated.

As mentioned above, in certain embodiments the applicators of the invention may be configured to react polyalkyleneimines, or other amine-containing polymers, with cross-linking agents, to form hydrogels. A large number of cross-linking agents are amenable to the invention. In certain instances, the cross-linking agent is an activated polyethylene glycol. The activating group is preferably an electrophilic group. For example, in certain instances, the polyethylene glycol contains a N-hydroxysuccinimide group at each end of the polymer. In certain instances, the succinimide is functionalized with a sulfonic acid moiety. In certain instances, the polyethylene glycol contains an aldehyde at each end of the polyethylene glycol. In certain instances the polyethylene glycol is a star, dendritic, or branched polymer with three or more activating groups.

In certain instances, the polyethylene glycol cross-linking agent contains two or more different electrophiles. The different electrophiles may have similar or dissimilar reactivities. The different electrophiles provide linkages having similar or dissimilar degradation rates. The selection of electrophiles allows for control over the crosslinking reactions to form the hydrogels, the adhesive properties, and the degradation rate of the formed hydrogel. For example, a polyethylene glycol can be derivatized such that one end of the polyethylene glycol contains a SPA and another end contains a SG. In this example, both are activated esters, but the degradation rates of the two linkages are different. For example, a hydrogel prepared with only a PEG-SPA is generally stable at 37° C. for more than about four months, whereas a hydrogel prepared with PEG-SG is often stable for less than about one week. Notably, one hydrogel prepared from PEI and a PEG-SPA/SG having a 60:40 ratio of SPA:SG degraded in about a week.

In certain instance, more than one polyethylene glycol cross-liking agents can be used. For example, a mixture of PEI/PEG-SPA and PEI/PEG-SG. The different cross-linkers may provide linkages having similar or dissimilar degradation rates, and thus the properties of the resulting hydrogel can be controlled.

In certain instances, the polyethylene glycol cross-linking agent contains a hydrophobic moiety. In certain instances, alkyl groups are installed between the polyethylene glycol and the terminal electrophilic groups of the cross-linking agent. In certain instances, the alkyl group contains about 4 to about 30 carbon atoms. In certain instances, the alkyl group contains about 5 to about 15 carbon atoms. In certain instances, the hydrophobic moiety is an aryl or aralkyl group. In certain instances, the alkyl moiety of the aralkyl group contains between 5-10 carbon atoms.

In certain instances, the polyethylene glycol cross-linking agent is represented by the generic formula (i) below, wherein w is an integer in the range of about 5 to 10,000, and n is an integer in the range of about 5 to about 30.

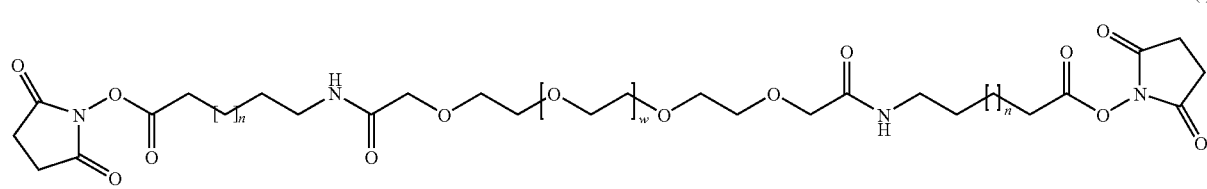

(i)

In certain instances, the polyethylene glycol cross-linking agent is represented by the generic formula (ii) below, wherein w is an integer in the range of about 5 to 10,000, and m is an integer in the range of about 1 to about 50.

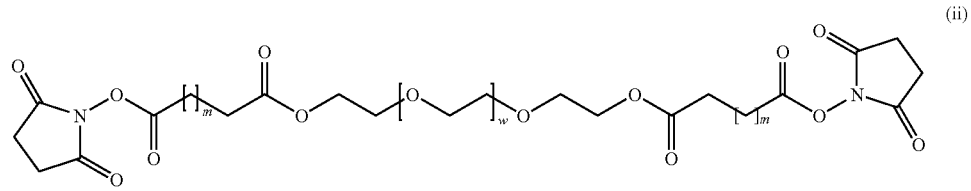

(ii)

In certain instances the hydrophobic moiety may be used as a foaming agent. The linkages between the polyethylene glycol and the hydrophobic moiety can be esters, amides, carbamates, carbonates, urea, urethane, and so forth.

A further embodiment of the invention is an applicator, and methods of use thereof, for chemical peptide ligation reactions, to create a crosslinked gel involving a dendritic polymer. In this reaction an aldehyde, aldehyde-acid or aldehyde-ester reacts with a cysteine-functionalized polymer to form a gel or crosslinked network. In certain instances, the dendritic polymers have nucleophilic groups, such as primary amino groups or thiol groups, which can react with electrophilic groups, such as an acrylate, succinimidyl ester, maleimide, ester aldehyde, or aldehyde on a small molecule. In certain instances, the dendritic polymer has nucleophilic groups capable of reacting with an activated diester of sebacic acid.

In certain embodiments it was noticed that material would leak from the end of the applicator for a short time after pressure had ceased to be applied to the plungers. Not intending to be bound by any one theory, it was hypothesised that air, both dissolved air and foaminess within the reconstituted material (e.g., activated PEG), was compressed during the application phase and then resulted in expression of some small amount of reconstituted component after stopping. Removing the filters in some embodiments made this phenomena stop, pointing towards verification of the hypothesis. With regards to activated PEG, it was further known that the current recrystallization method yields a fluffy powder that has a fairly low bulk density of approximately 0.25 g/cc. It was theorized that if fairly dense but small particles of PEG were used that one could reduce the amount of air in the reconstituted PEG and thus reduce the unintended delivery of reconstituted PEG after stopping. Examples of denser PEG materials are described in Example 10 below.

Selected Applicators

One aspect of the invention relates to an applicator comprising a housing and a nozzle assembly; wherein
(i) the housing comprises
a first barrel, comprising a first diameter, a first end, and a second end;
a first internal chamber, comprising a proximal end and a distal end;
a second internal chamber, comprising a proximal end and a distal end;
a first floating plunger, located within the first barrel and under pressure movable therethrough, separating the first internal chamber from the second internal chamber, thereby forming the distal end of the first internal chamber, and the proximal end of the second internal chamber;
a first plunger, comprising a first end and a second end, the second end of the first plunger is located at least partially within the first end of the first barrel and under pressure movable therethrough, thereby forming the proximal end of the first internal chamber;
a first fluid bypass, located on the first barrel, external to the second internal chamber;
a first piercable barrier, located at the distal end of the second internal chamber;
a second barrel comprising a second diameter, a first end, and a second end;
a third internal chamber, comprising a proximal end and a distal end;
a fourth internal chamber, comprising a proximal end and a distal end;
a second floating plunger, located within the second barrel and under pressure movable therethrough, separating the third internal chamber from the fourth internal chamber, thereby forming the distal end of the third internal chamber, and the proximal end of the fourth internal chamber;
a second plunger, comprising a first end and a second end, the second end of the second plunger is located at least partially within the first end of the second barrel and under pressure movable therethrough, thereby forming the proximal end of the third internal chamber;
a second fluid bypass, located on the second barrel, external to the fourth internal chamber;
a second piercable barrier, located at the distal end of the fourth internal chamber;
(ii) the nozzle assembly comprises
a first inlet and a first piercer, wherein the first piercer is suitably positioned to pierce the first piercable barrier, and thereby connect the first inlet to the second internal chamber; and the
a second inlet and a second piercer, wherein the second piercer is suitably positioned to pierce the second piercable barrier, and thereby connect the second inlet to the fourth internal chamber;
a gas inlet; and
an outlet in fluid communication with the first inlet, the second inlet and the gas inlet.

In certain embodiments, the present invention relates to any one of the aforementioned applicators, wherein the applicator further comprises a drive train and a locking mechanism;
the drive train comprises a motor and a gear train, wherein the motor is connected to the gear train; the gear train is attached to the first end of the first plunger; and the gear train is attached to the first end of the second plunger; and
the lock mechanism is initially positioned to prevent the housing from substantially moving towards the nozzle assembly, thereby initially preventing the first piercer from piercing the first piercable barrier and initially preventing the second piercer from piercing the second piercable barrier.

In certain embodiments, the present invention relates to any one of the aforementioned applicators, wherein the applicator body further comprises a liquid in the first internal chamber.

In certain embodiments, the present invention relates to any one of the aforementioned applicators, wherein the applicator body further comprises a liquid in the first internal chamber; and the applicator has a sterility assurance level of between about $10^{-3}$ to about $10^{-6}$.

In certain embodiments, the present invention relates to any one of the aforementioned applicators, wherein the applicator body further comprises a liquid in the first internal chamber; and the liquid is a buffer.

In certain embodiments, the present invention relates to any one of the aforementioned applicators, wherein the applicator body further comprises a liquid in the third internal chamber.

In certain embodiments, the present invention relates to any one of the aforementioned applicators, wherein the applicator body further comprises a liquid in the third internal chamber; and the applicator has a sterility assurance level of between about $10^{-3}$ to about $10^{-6}$.

In certain embodiments, the present invention relates to any one of the aforementioned applicators, wherein the applicator body further comprises a liquid in the third internal chamber; and the liquid is a buffer.

In certain embodiments, the present invention relates to any one of the aforementioned applicators, wherein the applicator body further comprises a viscous liquid in the second internal chamber.

In certain embodiments, the present invention relates to any one of the aforementioned applicators, wherein the applicator body further comprises a viscous liquid in the second internal chamber; and the applicator has a sterility assurance level of between about $10^{-3}$ to $10^{-6}$.

In certain embodiments, the present invention relates to any one of the aforementioned applicators, wherein the applicator body further comprises a viscous liquid in the second internal chamber; and the viscous liquid comprises a polyalkyleneimine.

In certain embodiments, the present invention relates to any one of the aforementioned applicators, wherein the applicator body further comprises a viscous liquid in the second internal chamber; and the viscous liquid comprises PEI.

In certain embodiments, the present invention relates to any one of the aforementioned applicators, wherein the applicator body further comprises a solid in the fourth internal chamber; and the solid comprises an activated PEG.

In certain embodiments, the present invention relates to any one of the aforementioned applicators, wherein the bulk density of the activated PEG is between about 0.1 g/cc and 0.2 g/cc. In certain embodiments, the present invention relates to any one of the aforementioned applicators, wherein the bulk density of the activated PEG is between about 0.2 g/cc and 0.3 g/cc. In certain embodiments, the present invention relates to any one of the aforementioned applicators, wherein the bulk density of the activated PEG is between about 0.3 g/cc and 0.4 g/cc. In certain embodiments, the present invention relates to any one of the aforementioned applicators, wherein the bulk density of the activated PEG is between about 0.4 g/cc and 0.5 g/cc. In certain embodiments, the present invention relates to any one of the aforementioned applicators, wherein the bulk density of the activated PEG is between about 0.5 g/cc and 0.6 g/cc. In certain embodiments, the present invention relates to any one of the aforementioned applicators, wherein the bulk density of the activated PEG is between about 0.7 g/cc and 0.8 g/cc. In certain embodiments, the present invention relates to any one of the aforementioned applicators, wherein the bulk density of the activated PEG is between about 0.9 g/cc and 1 g/cc. In certain embodiments, the present invention relates to any one of the aforementioned applicators, wherein the bulk density of the activated PEG is between about 1 g/cc and 10 g/cc.

In certain embodiments, the present invention relates to any one of the aforementioned applicators, wherein the applicator body further comprises a solid in the fourth internal chamber; the solid comprises an activated PEG; and the activated PEG is a star, dendritic, or branched polymer with between three and less than twenty activating groups.

In certain embodiments, the present invention relates to any one of the aforementioned applicators, wherein the applicator body further comprises a solid in the fourth internal chamber; and the solid comprises

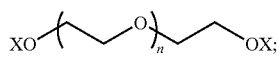

wherein n is 10-200 inclusive; and X is —$CH_2C(=O)O$(N-succinimidyl), —$(CH_2)_2C(=O)O$(N-succinimidyl), —$(CH_2)_3C(=O)O$(N-succinimidyl), —$(CH_2)_4C(=O)O$(N-succinimidyl), —$(CH_2)_5C(=O)O$(N-succinimidyl), —$(CH_2)_6C(=O)O$(N-succinimidyl), —$(CH_2)_7C(=O)O$(N-succinimidyl), —$(CH_2)_8C(=O)O$(N-succinimidyl), —$(CH_2)_9C(=O)O$(N-succinimidyl), —$C(=O)CH_2C(=O)O$(N-succinimidyl), —$C(=O)(CH_2)_2C(=O)O$(N-succinimidyl), —$C(=O)(CH_2)_3C(=O)O$(N-succinimidyl), —$C(=O)(CH_2)_4C(=O)O$(N-succinimidyl), —$C(=O)(CH_2)_5C(=O)O$(N-succinimidyl), —$C(=O)(CH_2)_6C(=O)O$(N-succinimidyl), —$C(=O)(CH_2)_7C(=O)O$(N-succinimidyl), —$C(=O)(CH_2)_8C(=O)O$(N-succinimidyl), or —$C(=O)(CH_2)_9C(=O)O$(N-succinimidyl).

In certain embodiments, the present invention relates to any one of the aforementioned applicators, wherein the applicator body further comprises a solid in the fourth internal chamber; and the solid is

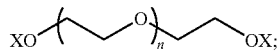

wherein n is 80-120 inclusive; and X is —$(CH_2)_3C(=O)O$(N-succinimidyl), —$C(=O)(CH_2)_3C(=O)O$(N-succinimidyl), or —$C(=O)(CH_2)_8C(=O)O$(N-succinimidyl).

In certain embodiments, the present invention relates to any one of the aforementioned applicators, wherein the housing further comprises a first pressure valve, located on the first barrel, external to the second internal chamber.

In certain embodiments, the present invention relates to any one of the aforementioned applicators, wherein the housing further comprises a second pressure valve, located on the second barrel, external to the fourth internal chamber.

In certain embodiments, the present invention relates to any one of the aforementioned applicators, wherein the housing further comprises a first hydrophobic filter, located at or near the distal end of the second internal chamber.

In certain embodiments, the present invention relates to any one of the aforementioned applicators, wherein the housing further comprises a second hydrophobic filter, located at or near the distal end of the fourth internal chamber.

In certain embodiments, the present invention relates to any one of the aforementioned applicators, wherein the housing further comprises a first check valve, located at or near the distal end of the second internal chamber. In certain embodiments, the present invention relates to any one of the aforementioned applicators, wherein the first check valve is a duck bill valve, rubber dome valve or bi-directional valve. With regard to choosing a check valve, it can be advantageous to have a moderate cracking pressure, a positive shut off and still allow relatively high flow rates when the valve is opened.

In certain embodiments, the present invention relates to any one of the aforementioned applicators, wherein the housing further comprises a second check valve, located at or near the distal end of the fourth internal chamber. In certain embodiments, the present invention relates to any one of the aforementioned applicators, wherein the second check valve is a duck bill valve, rubber dome valve or bi-directional valve. In certain embodiments, the present invention relates to any one of the aforementioned applicators, wherein the first plunger comprises rubber. In certain embodiments, the present invention relates to any one of the aforementioned applicators, wherein the first plunger comprises bromobutyl rubber. In certain embodiments, the first plunger further comprises a coating of lubricant. In certain embodiments, the lubricant is a medical grade silicone lubricant.

In certain embodiments, the present invention relates to any one of the aforementioned applicators, wherein the second plunger comprises rubber. In certain embodiments, the present invention relates to any one of the aforementioned applicators, wherein the second plunger comprises bromobutyl rubber. In certain embodiments, the second plunger further comprises a coating of lubricant. In certain embodiments, the lubricant is a medical grade silicone lubricant.

In certain embodiments, the present invention relates to any one of the aforementioned applicators, wherein the nozzle is designed so that gas entering the gas inlet combines with material from the first inlet before the resulting mixture combines with material from the second inlet.

In certain embodiments, the present invention relates to any one of the aforementioned applicators, wherein the nozzle is designed so that gas entering the gas inlet combines with material from the second inlet before the resulting mixture combines with material from the first inlet.

In certain embodiments, the present invention relates to any one of the aforementioned applicators, wherein the nozzle further comprises a brush, a sponge, a foam swab, a porous plastic component, a duck bill tip, a textile mitt or a spray tip affixed to the outlet.

In certain embodiments, the present invention relates to any one of the aforementioned applicators, wherein the nozzle further comprises a tubular fitment comprising two open ends; one end of the tubular fitment is affixed to the outlet; and the tubular fitment is adapted to pass through an endoscope or a laparoscope.

In certain embodiments, the present invention relates to any one of the aforementioned applicators, wherein the nozzle further comprises a tubular fitment comprising two open ends; one open end of the tubular fitment is affixed to the outlet and the other open end of the fitment has a flattened opening relative to the open end affixed to the outlet.

In certain embodiments, the present invention relates to any one of the aforementioned applicators, wherein the nozzle further comprises a tubular fitment comprising two open ends; one open end of the tubular fitment is affixed to the outlet and the other open end of the fitment comprises a protruding spatula-like piece.

In certain embodiments, the present invention relates to any one of the aforementioned applicators, wherein said applicator is shaped like a pen.

In certain embodiments, the present invention relates to any one of the aforementioned applicators, wherein said applicator is shaped like a gun.

In certain embodiments, the present invention relates to any one of the aforementioned applicators, wherein said applicator is shaped like a gun; and the applicator further comprises a pistol-style grip.

In certain embodiments, the present invention relates to any one of the aforementioned applicators, further comprising an atomization fluid pathway.

In certain embodiments, the present invention relates to any one of the aforementioned applicators, further comprising an atomization fluid pathway; wherein said atomization fluid pathway is configured to expel any material in the nozzle out of the nozzle through the outlet.

In certain embodiments, the present invention relates to any one of the aforementioned applicators, further comprising an air pump.

In certain embodiments, the present invention relates to any one of the aforementioned applicators, further comprising an air pump and an air filter. In certain embodiments, the present invention relates to any one of the aforementioned applicators, further comprising an air pump and an air filter, wherein the air filter has a pore size of less than about 1.0 microns. In certain embodiments, the present invention relates to any one of the aforementioned applicators, further comprising an air pump and an air filter, wherein the air filter has a pore size of less than about 0.5 microns. In certain embodiments, the present invention relates to any one of the aforementioned applicators, further comprising an air pump and an air filter, wherein the air filter has a pore size of less than about 0.4 microns. In certain embodiments, the present invention relates to any one of the aforementioned applicators, further comprising an air pump and an air filter, wherein the air filter has a pore size of less than about 0.3 microns. In certain embodiments, the present invention relates to any one of the aforementioned applicators, further comprising an air pump and an air filter, wherein the air filter has a pore size of less than about 0.2 microns.

In certain embodiments, the present invention relates to any one of the aforementioned applicators, wherein the air pump comprises an inlet end and a discharge end, and is battery operated.

In certain embodiments, the present invention relates to any one of the aforementioned applicators, wherein the air pump is contained within a housing which further comprises batteries and an adapter at the discharge end of the air pump.

In certain embodiments, the present invention relates to any one of the aforementioned applicators, wherein the air pump is contained within an air pump housing which further comprises batteries and an adapter at the discharge end of the air pump; and the discharge end of the air pump is in fluid communication with the gas inlet of the nozzle assembly.

In certain embodiments, the present invention relates to any one of the aforementioned applicators, wherein the adapter at the discharge end of the air pump is a luer lock adapter.

In certain embodiments, the present invention relates to any one of the aforementioned applicators, further comprising an air pump; and further comprising an ultraviolet light source designed to kill germs or pathogens within the air stream. In certain embodiments, the present invention relates to any of the aforementioned applicators, wherein the ultraviolet light source is an UV emitting LED.

In certain embodiments, the present invention relates to any one of the aforementioned applicators, wherein the material in the nozzle is atomized by compressed air, nitrogen, argon or carbon dioxide.

In certain embodiments, the present invention relates to any one of the aforementioned applicators, further comprising a piezoelectric atomizer.

In certain embodiments, the present invention relates to any one of the aforementioned applicators, wherein the material in the nozzle is atomized by the piezoelectric atomizer.

In certain embodiments, the present invention relates to any one of the aforementioned applicators, further comprising a trigger mechanism.

In certain embodiments, the present invention relates to any one of the aforementioned applicators, wherein activating the trigger mechanism starts the drive train, thereby compressing the first plunger and the second plunger and opening the first fluid bypass and the second fluid bypass.

In certain embodiments, the present invention relates to any one of the aforementioned applicators, further comprising analog circuitry.

Figure 7:
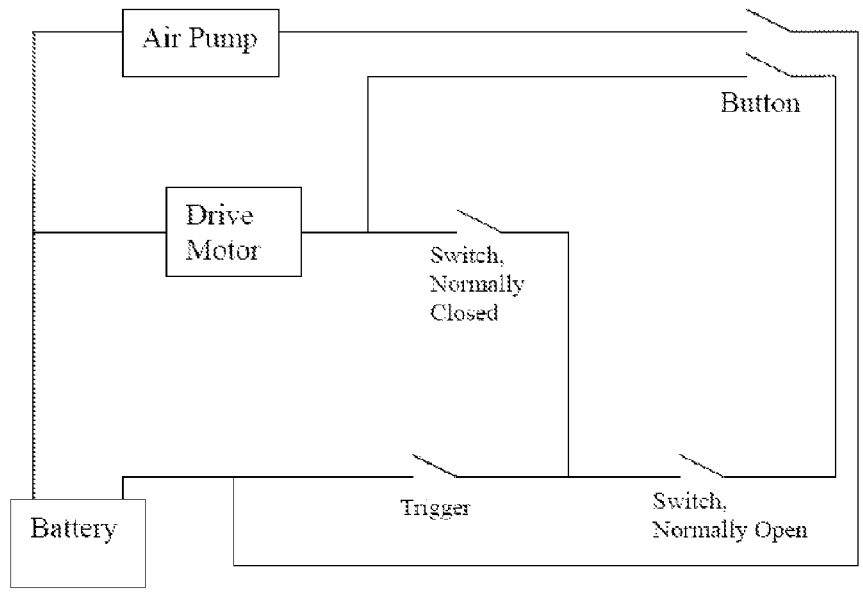
FIGS. 7 [A] and [B] depict analog circuit diagrams.
Figure 7:
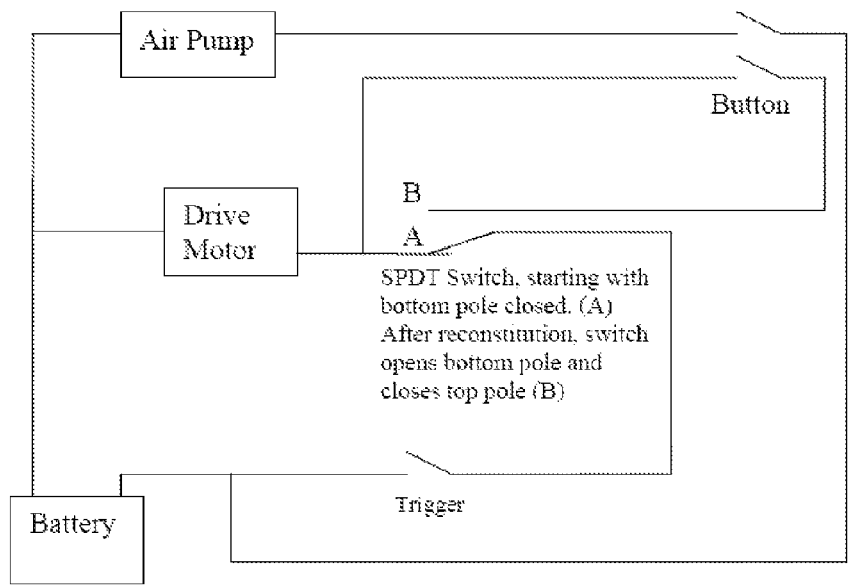

In certain embodiments, the present invention relates to any one of the aforementioned applicators, further comprising analog circuitry, e.g., as depicted in FIG. 7 (top or bottom).

In certain embodiments, the present invention relates to any one of the aforementioned applicators, further comprising a discrete logic board.

In certain embodiments, the present invention relates to any one of the aforementioned applicators, further comprising an integrated circuit.

In certain embodiments, the present invention relates to any one of the aforementioned applicators, further comprising an integrated circuit and a programmable logic controller.

In certain embodiments, the present invention relates to any one of the aforementioned applicators, further comprising a trigger mechanism, an integrated circuit, and a programmable logic controller, wherein activating the trigger mechanism engages a contact switch, thereby signaling to the programmable logic controller that the trigger mechanism has been activated.

In certain embodiments, the present invention relates to any one of the aforementioned applicators, further comprising a trigger mechanism, an integrated circuit, and a programmable logic controller, wherein activating the trigger mechanism engages a contact switch; and engaging the contact switch starts the drive train, thereby compressing the first plunger and the second plunger.

In certain embodiments, the present invention relates to any one of the aforementioned applicators, further comprising a trigger mechanism which controls the movement of one or more plungers; and the trigger comprises a button.

In certain embodiments, the present invention relates to any one of the aforementioned applicators, further comprising a power source, wherein said power source is contained within the applicator.

In certain embodiments, the present invention relates to any one of the aforementioned applicators, further comprising a power source, wherein said power source is outside of the applicator.

In certain embodiments, the present invention relates to any one of the aforementioned applicators, further comprising a plug suitable for connection to a power source.

In certain embodiments, the present invention relates to any one of the aforementioned applicators, further comprising a power source, wherein said power source is selected from the group consisting of compressed gas, mechanical power, chemical power, or electrical power.

In certain embodiments, the present invention relates to any one of the aforementioned applicators, further comprising a means to use chemical power as a power source.

In certain embodiments, the present invention relates to any one of the aforementioned applicators, further comprising a means to use manual power as a power source.

In certain embodiments, the present invention relates to any one of the aforementioned applicators, further comprising a power source, wherein said power source is contained within the applicator; and said power source comprises a battery.

In certain embodiments, the present invention relates to any one of the aforementioned applicators, further comprising a power source and a means for activating the power source, wherein said power source is contained within the applicator; said power source comprises a battery; and the means for activating the power source is a switch.

In certain embodiments, the present invention relates to any one of the aforementioned applicators, further comprising a power source and a means for activating the power source, wherein said power source is contained within the applicator; said power source comprises a battery; and the means for activating the power source is a pull tab.

In certain embodiments, the present invention relates to any one of the aforementioned applicators, wherein the first piercable barrier comprises one or more polymers selected from the group consisting of polyacrylics, silicones, polyolefins, polystyrenes, polyesters, polyethers, polyurethanes, polycarbonates, polyamines, or co-polymers thereof.

In certain embodiments, the present invention relates to any one of the aforementioned applicators, wherein the first piercable barrier comprises a metal-containing laminate.

In certain embodiments, the present invention relates to any one of the aforementioned applicators, wherein the exterior surface of the first piercable barrier is paper coated with wax or plastic.

In certain embodiments, the present invention relates to any one of the aforementioned applicators, wherein the second piercable barrier comprises one or more polymers selected from the group consisting of polyacrylics, silicones, polyolefins, polystyrenes, polyesters, polyethers, polyurethanes, polycarbonates, polyamines, or co-polymers thereof.

In certain embodiments, the present invention relates to any one of the aforementioned applicators, wherein the second piercable barrier comprises a metal.

In certain embodiments, the present invention relates to any one of the aforementioned applicators, wherein the exterior surface of the second piercable barrier is paper coated with wax or plastic.

In certain embodiments, the present invention relates to any one of the aforementioned applicators, further comprising a means of vibrating the housing.

In certain embodiments, the present invention relates to any one of the aforementioned applicators, wherein the means of vibrating the housing is a piezoelectric vibrator.

In certain embodiments, the present invention relates to any one of the aforementioned applicators, wherein the means of vibrating the housing is an electric motor vibrator.

In certain embodiments, the present invention relates to any one of the aforementioned applicators, wherein the housing further comprises a third barrel.

In certain embodiments, the present invention relates to any one of the aforementioned applicators, wherein the third barrel further comprises a third plunger, a third floating plunger, a third fluid bypass, and a third pressure valve between the distal end of the third barrel and the third floating plunger.

In certain embodiments, the present invention relates to any one of the aforementioned applicators, wherein the third plunger comprises rubber. In certain embodiments, the present invention relates to any one of the aforementioned applicators, wherein the third plunger comprises bromobutyl rubber. In certain embodiments, the third plunger further comprises a coating of lubricant. In certain embodiments, the lubricant is a medical grade silicone lubricant.

In certain embodiments, the present invention relates to any one of the aforementioned applicators, wherein the third barrel further comprises a third plunger, a third floating plunger, a third fluid bypass, and a third hydrophobic filter at or near the distal end of the third barrel.

In certain embodiments, the present invention relates to any one of the aforementioned applicators, wherein the third barrel further comprises a third floating plunger, a third fluid bypass, and a third check valve at or near the distal end of the third barrel. In certain embodiments, the present invention relates to any one of the aforementioned applicators, wherein the third check valve is a rubber dome valve or bi-directional valve.

In certain embodiments, the present invention relates to any one of the aforementioned applicators, further comprising an indicator light.

In certain embodiments, the present invention relates to any one of the aforementioned applicators, further comprising an indicator light, wherein the indicator light is a light emitting diode.

In certain embodiments, the present invention relates to any one of the aforementioned applicators, wherein the first plunger and the second plunger are mechanically locked such that their ability to advance through the first barrel and the second barrel, respectively, is constrained to be substantially in unison.

In certain embodiments, the present invention relates to any one of the aforementioned applicators, wherein the length of the first barrel is between about 0.5 inches to about 9 inches; or about 1.5 inches to about 4 inches; or about 2 inches to about 3 inches.

In certain embodiments, the present invention relates to any one of the aforementioned applicators, wherein the diameter of the first barrel is between about 0.2 inches and about 2 inches; or about 0.3 inches to about 0.75 inches; or about 0.4 inches to about 0.6 inches.

In certain embodiments, the present invention relates to any one of the aforementioned applicators, wherein the length of the second barrel is between about 0.5 inches to about 9 inches; or about 1.5 inches to about 4 inches; or about 2 inches to about 3 inches.

In certain embodiments, the present invention relates to any one of the aforementioned applicators, wherein the diameter of the second barrel is between about 0.2 inches and about 2 inches; or about 0.3 inches to about 0.75 inches; or about 0.4 inches to about 0.6 inches.

By proper sizing of orifices at the distal end of the housing, even without seals at the distal end of the housing, one can prevent inadvertent leaking of the reconstituted material, e.g., reconstituted PEG or reconstituted PEI solutions, prior to use. In certain embodiments, the present invention relates to any one of the aforementioned applicators, wherein the distal end of the second internal chamber has a first opening which has a diameter between about 0.1 inches and about 1 inch; or about 0.15 inches to about 0.38 inches; or about 0.2 inches to about 0.3 inches; or about 0.05 inches and about 0.5 inches; or about 0.08 inches to about 0.19 inches; or about 0.1 inches to about 0.15 inches; or about 0.01 inches and about 0.1 inch; or about 0.02 inches to about 0.04 inches.

In certain embodiments, the present invention relates to any one of the aforementioned applicators, wherein the distal end of the fourth internal chamber has a second opening which has a diameter between about 0.1 inches and about 1 inch; or about 0.15 inches to about 0.38 inches; or about 0.2 inches to about 0.3 inches; or about 0.05 inches and about 0.5 inches; or about 0.08 inches to about 0.19 inches; or about 0.1 inches to about 0.15 inches; or about 0.01 inches and about 0.1 inch; or about 0.02 inches to about 0.04 inches.

In certain embodiments, the present invention relates to any one of the aforementioned applicators, wherein the length of the nozzle assembly is between about 0.5 inches and about 15 inches; or about 0.75 inches to about 6 inches; or about 1 inch to about 2 inches.

In certain embodiments, the present invention relates to any one of the aforementioned applicators, wherein the diameter of the outlet is between about 0.001 inches and about 1 inch; or about 0.01 inches to about 0.05 inches; or about 0.01 inches to about 0.04 inches; or about 0.01 inches to about 0.03 inches; or about 0.01 inches to about 0.02 inches.

In certain embodiments, the present invention relates to any one of the aforementioned applicators, wherein instead of a fluid bypass, the floating plunger head contains a check valve which, when opened, connects the chambers in a given barrel.

In certain embodiments, the present invention relates to any one of the aforementioned applicators, wherein instead of a floating plunger and bypass, a hydrophobic septum is used.

In certain embodiments, the present invention relates to any one of the aforementioned applicators, further comprising a third piercer on the first plunger; and a third piercable barrier between the first plunger and the floating plunger. In certain embodiments, the present invention relates to any one of the aforementioned applicators, wherein the third piercable barrier comprises one or more polymers selected from the group consisting of polyacrylics, silicones, polyolefins, polystyrenes, polyesters, polyethers, polyurethanes, polycarbonates, polyamines, or co-polymers thereof. In certain embodiments, the present invention relates to any one of the aforementioned applicators, wherein the third piercable barrier comprises a metal-containing laminate. In certain embodiments, the present invention relates to any one of the aforementioned applicators, wherein the exterior surface of the third piercable barrier is paper coated with wax or plastic.

In certain embodiments, the present invention relates to any one of the aforementioned applicators, further comprising a fourth piercer on the second plunger; and a fourth piercable barrier between the first plunger and the floating plunger. In certain embodiments, the present invention relates to any one of the aforementioned applicators, wherein the fourth piercable barrier comprises one or more polymers selected from the group consisting of polyacrylics, silicones, polyolefins, polystyrenes, polyesters, polyethers, polyurethanes, polycarbonates, polyamines, or co-polymers thereof. In certain embodiments, the present invention relates to any one of the aforementioned applicators, wherein the fourth piercable barrier comprises a metal-containing laminate. In certain embodiments, the present invention relates to any one of the aforementioned applicators, wherein the exterior surface of the fourth piercable barrier is paper coated with wax or plastic.

Selected Methods

One aspect of the invention relates to a method of using an applicator to apply a composition to a surface, wherein
the applicator comprises a housing and a nozzle assembly; wherein
(i) the housing comprises
a first barrel, comprising a first diameter, a first end, and a second end;
a first internal chamber, comprising a proximal end and a distal end;
a second internal chamber, comprising a proximal end and a distal end;
a first floating plunger, located within the first barrel and under pressure movable therethrough, separating the first internal chamber from the second internal chamber, thereby forming the distal end of the first internal chamber, and the proximal end of the second internal chamber;
a first plunger, comprising a first end and a second end, the second end of the first plunger is located at least partially within the first end of the first barrel and under pressure movable therethrough, thereby forming the proximal end of the first internal chamber;
a first fluid bypass, located on the first barrel, external to the second internal chamber;
a first piercable barrier, located at the distal end of the second internal chamber;

a second barrel comprising a second diameter, a first end, and a second end;

a third internal chamber, comprising a proximal end and a distal end;

a fourth internal chamber, comprising a proximal end and a distal end;

a second floating plunger, located within the second barrel and under pressure movable therethrough, separating the third internal chamber from the fourth internal chamber, thereby forming the distal end of the third internal chamber, and the proximal end of the fourth internal chamber;

a second plunger, comprising a first end and a second end, the second end of the second plunger is located at least partially within the first end of the second barrel and under pressure movable therethrough, thereby forming the proximal end of the third internal chamber;

a second fluid bypass, located on the second barrel, external to the fourth internal chamber;

a second piercable barrier, located at the distal end of the fourth internal chamber;

(ii) the nozzle assembly comprises a first inlet and a first piercer, wherein the first piercer is suitably positioned to pierce the first piercable barrier, and thereby connect the first inlet to the second internal chamber; and the a second inlet and a second piercer, wherein the second piercer is suitably positioned to pierce the second piercable barrier, and thereby connect the second inlet to the fourth internal chamber;

a gas inlet; and an outlet in fluid communication with the first inlet, the second inlet and the gas inlet;

(iii) the housing further comprises a first liquid in the first internal chamber, a second liquid in the third internal chamber, a viscous liquid in the second internal chamber, and a solid in the fourth internal chamber;

comprising the steps of:

advancing the first plunger towards the second end of the first barrel, thereby advancing the first floating plunger towards the second end of the first barrel and over the first fluid bypass, and placing the first internal chamber in fluid communication with the second internal chamber;

advancing the second plunger towards the second end of the second barrel, thereby advancing the second floating plunger towards the second end of the second barrel and over the second fluid bypass, and placing the third internal chamber in fluid communication with the fourth internal chamber;

substantially advancing the housing toward the nozzle assembly, thereby piercing the first piercable barrier with the first piercer and the second piercable barrier with the second piercer, placing the second internal chamber in fluid communication with the nozzle, placing the fourth internal chamber in fluid communication with the nozzle, and forming a pre-composition mixture in the nozzle; and applying the pre-composition mixture to the surface, wherein the mixture gels to form the composition on the surface.

In certain embodiments, the present invention relates to any one of the aforementioned methods, wherein the applicator further comprises a drive train and a locking mechanism;

the drive train comprises a motor and a gear train, wherein the motor is connected to the gear train; the gear train is attached to the first end of the first plunger; and the gear train is attached to the first end of the second plunger; and the lock mechanism is initially positioned to prevent the housing from substantially moving towards the nozzle assembly, thereby initially preventing the first piercer from piercing the first piercable barrier and initially preventing the second piercer from piercing the second piercable barrier.

In certain embodiments, the present invention relates to any one of the aforementioned methods, further comprising the step of agitating the housing to promote mixing of the first liquid with the first solid; and to promote mixing of the second liquid with the second solid; wherein the step of agitating the housing is completed after the first internal chamber is in fluid communication with the second internal chamber, and the third internal chamber is in fluid communication with the fourth internal chamber.

In certain embodiments, the present invention relates to any one of the aforementioned methods, wherein the step of agitating the housing comprises vibrating the housing.

In certain embodiments, the present invention relates to any one of the aforementioned methods, wherein the applicator has a sterility assurance level of between about $10^{-3}$ to about $10^{-6}$.

In certain embodiments, the present invention relates to any one of the aforementioned methods, wherein liquid in the first internal chamber is a buffer.

In certain embodiments, the present invention relates to any one of the aforementioned methods, wherein liquid in the third internal chamber is a buffer.

In certain embodiments, the present invention relates to any one of the aforementioned methods, wherein the viscous liquid in the second internal chamber comprises a polyalkyleneimine.

In certain embodiments, the present invention relates to any one of the aforementioned methods, wherein the viscous liquid in the second internal chamber comprises PEI.

In certain embodiments, the present invention relates to any one of the aforementioned methods, wherein the solid in the fourth internal chamber comprises an activated PEG.

In certain embodiments, the present invention relates to any one of the aforementioned methods, wherein the bulk density of the activated PEG is between about 0.1 g/cc and 0.2 g/cc. In certain embodiments, the present invention relates to any one of the aforementioned methods, wherein the bulk density of the activated PEG is between about 0.2 g/cc and 0.3 g/cc. In certain embodiments, the present invention relates to any one of the aforementioned methods, wherein the bulk density of the activated PEG is between about 0.3 g/cc and 0.4 g/cc. In certain embodiments, the present invention relates to any one of the aforementioned methods, wherein the bulk density of the activated PEG is between about 0.4 g/cc and 0.5 g/cc. In certain embodiments, the present invention relates to any one of the aforementioned methods, wherein the bulk density of the activated PEG is between about 0.5 g/cc and 0.6 g/cc. In certain embodiments, the present invention relates to any one of the aforementioned methods, wherein the bulk density of the activated PEG is between about 0.7 g/cc and 0.8 g/cc. In certain embodiments, the present invention relates to any one of the aforementioned methods, wherein the bulk density of the activated PEG is between about 0.9 g/cc and 1 g/cc. In certain embodiments, the present invention relates to any one of the aforementioned methods, wherein the bulk density of the activated PEG is between about 1 g/cc and 10 g/cc.

In certain embodiments, the present invention relates to any one of the aforementioned methods, wherein the solid in the fourth internal chamber comprises an activated PEG; and the activated PEG is a star, dendritic, or branched polymer with between three and less that twenty activating groups.

In certain embodiments, the present invention relates to any one of the aforementioned methods, wherein the solid in the fourth internal chamber comprises

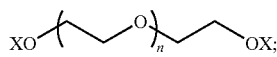

wherein n is 10-200 inclusive; and X is —CH$_2$C(=O)O(N-succinimidyl), —(CH$_2$)$_2$C(=O)O(N-succinimidyl), —(CH$_2$)$_3$C(=O)O(N-succinimidyl), —(CH$_2$)$_4$C(=O)O(N-succinimidyl), —(CH$_2$)$_5$C(=O)O(N-succinimidyl), —(CH$_2$)$_6$C(=O)O(N-succinimidyl), —(CH$_2$)$_7$C(=O)O(N-succinimidyl), —(CH$_2$)$_8$C(=O)O(N-succinimidyl), —(CH$_2$)$_9$C(=O)O(N-succinimidyl), —C(=O)CH$_2$C(=O)O(N-succinimidyl), —C(=O)(CH$_2$)$_2$C(=O)O(N-succinimidyl), —C(=O)(CH$_2$)$_3$C(=O)O(N-succinimidyl), —C(=O)(CH$_2$)$_4$C(=O)O(N-succinimidyl), —C(=O)(CH$_2$)$_5$C(=O)O(N-succinimidyl), —C(=O)(CH$_2$)$_6$C(=O)O(N-succinimidyl), —C(=O)(CH$_2$)$_7$C(=O)O(N-succinimidyl), —C(=O)(CH$_2$)$_8$C(=O)O(N-succinimidyl), or —C(=O)(CH$_2$)$_9$C(=O)O(N-succinimidyl).

In certain embodiments, the present invention relates to any one of the aforementioned methods, wherein the solid in the fourth internal chamber comprises

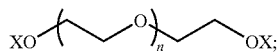

wherein n is 80-120 inclusive; and X is —(CH$_2$)$_3$C(=O)O(N-succinimidyl), —C(=O)(CH$_2$)$_3$C(=O)O(N-succinimidyl), or —C(=O)(CH$_2$)$_8$C(=O)O(N-succinimidyl).

In certain embodiments, the present invention relates to any one of the aforementioned methods, wherein the housing further comprises a first pressure valve, located on the first barrel, external to the second internal chamber.

In certain embodiments, the present invention relates to any one of the aforementioned methods, wherein the housing further comprises a second pressure valve, located on the second barrel, external to the fourth internal chamber.

In certain embodiments, the present invention relates to any one of the aforementioned methods, wherein the housing further comprises a first hydrophobic filter, located at or near the distal end of the second internal chamber.

In certain embodiments, the present invention relates to any one of the aforementioned methods, wherein the housing further comprises a second hydrophobic filter, located at or near the distal end of the fourth internal chamber.

In certain embodiments, the present invention relates to any one of the aforementioned methods, wherein the housing further comprises a first check valve, located at or near the distal end of the second internal chamber. In certain embodiments, the present invention relates to any one of the aforementioned methods, wherein the first check valve is a duck bill valve, rubber dome valve or bi-directional valve.

In certain embodiments, the present invention relates to any one of the aforementioned methods, wherein the housing further comprises a second check valve, located at or near the distal end of the fourth internal chamber. In certain embodiments, the present invention relates to any one of the aforementioned methods, wherein the second check valve is a duck bill valve, rubber dome valve or bi-directional valve. In certain embodiments, the present invention relates to any one of the aforementioned methods, wherein the first plunger comprises rubber. In certain embodiments, the present invention relates to any one of the aforementioned methods, wherein the first plunger comprises bromobutyl rubber. In certain embodiments, the first plunger further comprises a coating of lubricant. In certain embodiments, the lubricant is a medical grade silicone lubricant.

In certain embodiments, the present invention relates to any one of the aforementioned methods, wherein the second plunger comprises rubber. In certain embodiments, the present invention relates to any one of the aforementioned methods, wherein the second plunger comprises bromobutyl rubber. In certain embodiments, the second plunger further comprises a coating of lubricant. In certain embodiments, the lubricant is a medical grade silicone lubricant.

In certain embodiments, the present invention relates to any one of the aforementioned methods, wherein the nozzle is designed so that gas entering the gas inlet combines with material from the first inlet before the resulting mixture combines with material from the second inlet.

In certain embodiments, the present invention relates to any one of the aforementioned methods, wherein the nozzle is designed so that gas entering the gas inlet combines with material from the second inlet before the resulting mixture combines with material from the first inlet.

In certain embodiments, the present invention relates to any one of the aforementioned methods, wherein the nozzle further comprises a brush, a sponge, a foam swab, a porous plastic component, a duck bill tip, a textile mitt or a spray tip affixed to the outlet.

In certain embodiments, the present invention relates to any one of the aforementioned methods, wherein the nozzle further comprises a tubular fitment comprising two open ends; one end of the tubular fitment is affixed to the outlet; and the tubular fitment is adapted to pass through an endoscope or a laparoscope.

In certain embodiments, the present invention relates to any one of the aforementioned methods, wherein the nozzle further comprises a tubular fitment comprising two open ends; one open end of the tubular fitment is affixed to the outlet and the other open end of the fitment has a flattened opening relative to the open end affixed to the outlet.

In certain embodiments, the present invention relates to any one of the aforementioned methods, wherein the nozzle further comprises a tubular fitment comprising two open ends; one open end of the tubular fitment is affixed to the outlet and the other open end of the fitment comprises a protruding spatula-like piece.

In certain embodiments, the present invention relates to any one of the aforementioned methods, wherein said applicator is shaped like a pen.

In certain embodiments, the present invention relates to any one of the aforementioned methods, wherein said applicator is shaped like a gun.

In certain embodiments, the present invention relates to any one of the aforementioned methods, wherein said applicator is shaped like a gun; and the applicator further comprises a pistol-style grip.

In certain embodiments, the present invention relates to any one of the aforementioned methods, wherein the applicator further comprises an atomization fluid pathway.

In certain embodiments, the present invention relates to any one of the aforementioned methods, wherein the applicator further comprises an atomization fluid pathway; wherein said atomization fluid pathway is configured to expel any material in the nozzle out of the nozzle through the outlet.

In certain embodiments, the present invention relates to any one of the aforementioned methods, wherein the applicator further comprises an air pump.

In certain embodiments, the present invention relates to any one of the aforementioned methods, wherein the applicator further comprises an air pump and an air filter. In certain embodiments, the present invention relates to any one of the aforementioned methods, wherein the applicator further comprises an air pump and an air filter, wherein the air filter has a pore size of less than about 1.0 microns. In certain embodiments, the present invention relates to any one of the aforementioned methods, wherein the applicator further comprises an air pump and an air filter, wherein the air filter has a pore size of less than about 0.5 microns. In certain embodiments, the present invention relates to any one of the aforementioned methods, wherein the applicator further comprises an air pump and an air filter, wherein the air filter has a pore size of less than about 0.4 microns. In certain embodiments, the present invention relates to any one of the aforementioned methods, wherein the applicator further comprises an air pump and an air filter, wherein the air filter has a pore size of less than about 0.3 microns. In certain embodiments, the present invention relates to any one of the aforementioned methods, wherein the applicator further comprises an air pump and an air filter, wherein the air filter has a pore size of less than about 0.2 microns.

In certain embodiments, the present invention relates to any one of the aforementioned methods, wherein the air pump comprises an inlet end and a discharge end, and is battery operated.

In certain embodiments, the present invention relates to any one of the aforementioned methods, wherein the air pump is contained within a housing which further comprises batteries and an adapter at the discharge end of the air pump.

In certain embodiments, the present invention relates to any one of the aforementioned methods, wherein the air pump is contained within an air pump housing which further comprises batteries and an adapter at the discharge end of the air pump; and the discharge end of the air pump is in fluid communication with the gas inlet of the nozzle assembly.

In certain embodiments, the present invention relates to any one of the aforementioned methods, wherein the adapter at the discharge end of the air pump is a luer lock adapter.

In certain embodiments, the present invention relates to any one of the aforementioned methods, wherein the applicator further comprises an air pump; and the applicator further comprises an ultraviolet light source designed to kill germs or pathogens within the air stream. In certain embodiments, the present invention relates to any of the aforementioned methods, wherein the ultraviolet light source is an UV emitting LED.

In certain embodiments, the present invention relates to any one of the aforementioned methods, wherein the material in the nozzle is atomized by compressed air, nitrogen, argon or carbon dioxide.

In certain embodiments, the present invention relates to any one of the aforementioned methods, wherein the applicator further comprises a piezoelectric atomizer.

In certain embodiments, the present invention relates to any one of the aforementioned methods, wherein the material in the nozzle is atomized by the piezoelectric atomizer.

In certain embodiments, the present invention relates to any one of the aforementioned methods, wherein the applicator further comprises a trigger mechanism.

In certain embodiments, the present invention relates to any one of the aforementioned methods, wherein activating the trigger mechanism starts the drive train, thereby compressing the first plunger and the second plunger and opening the first fluid bypass and the second fluid bypass.

In certain embodiments, the present invention relates to any one of the aforementioned methods, further comprising analog circuitry.

In certain embodiments, the present invention relates to any one of the aforementioned methods, further comprising analog circuitry, e.g., as depicted in FIG. 7 (top or bottom).

In certain embodiments, the present invention relates to any one of the aforementioned methods, further comprising a discrete logic board.

In certain embodiments, the present invention relates to any one of the aforementioned methods, wherein the applicator further comprises an integrated circuit.

In certain embodiments, the present invention relates to any one of the aforementioned methods, wherein the applicator further comprises an integrated circuit and a programmable logic controller.

In certain embodiments, the present invention relates to any one of the aforementioned methods, wherein the applicator further comprises a trigger mechanism, an integrated circuit, and a programmable logic controller, wherein activating the trigger mechanism engages a contact switch, thereby signaling to the programmable logic controller that the trigger mechanism has been activated.

In certain embodiments, the present invention relates to any one of the aforementioned methods, wherein the applicator further comprises a trigger mechanism, an integrated circuit, and a programmable logic controller, wherein activating the trigger mechanism engages a contact switch; and engaging the contact switch starts the drive train, thereby compressing the first plunger and the second plunger.

In certain embodiments, the present invention relates to any one of the aforementioned methods, wherein the applicator further comprises a trigger mechanism which controls the movement of one or more plungers; and the trigger comprises a button.

In certain embodiments, the present invention relates to any one of the aforementioned methods, wherein the applicator further comprises a power source, wherein said power source is contained within the applicator.

In certain embodiments, the present invention relates to any one of the aforementioned methods, wherein the applicator further comprises a power source, wherein said power source is outside of the applicator.

In certain embodiments, the present invention relates to any one of the aforementioned methods, wherein the applicator further comprises a plug suitable for connection to a power source.

In certain embodiments, the present invention relates to any one of the aforementioned methods, wherein the applicator further comprises a power source, wherein said power source is selected from the group consisting of compressed gas, mechanical power, chemical power, or electrical power.

In certain embodiments, the present invention relates to any one of the aforementioned methods, wherein the applicator further comprises a means to use chemical power as a power source.

In certain embodiments, the present invention relates to any one of the aforementioned methods, wherein the applicator further comprises a means to use manual power as a power source.

In certain embodiments, the present invention relates to any one of the aforementioned methods, wherein the applicator further comprises a power source, wherein said power source is contained within the applicator; and said power source comprises a battery.

In certain embodiments, the present invention relates to any one of the aforementioned methods, wherein the applicator further comprises a power source and a means for activating the power source, wherein said power source is contained within the applicator; said power source comprises a battery; and the means for activating the power source is a switch.

In certain embodiments, the present invention relates to any one of the aforementioned methods, wherein the applicator further comprises a power source and a means for activating the power source, wherein said power source is contained within the applicator; said power source comprises a battery; and the means for activating the power source is a pull tab.

In certain embodiments, the present invention relates to any one of the aforementioned methods, wherein the first piercable barrier comprises one or more polymers selected from the group consisting of polyacrylics, silicones, polyolefins, polystyrenes, polyesters, polyethers, polyurethanes, polycarbonates, polyamines, or co-polymers thereof.

In certain embodiments, the present invention relates to any one of the aforementioned methods, wherein the first piercable barrier comprises a metal-containing laminate.

In certain embodiments, the present invention relates to any one of the aforementioned methods, wherein the exterior surface of the first piercable barrier is paper coated with wax or plastic.

In certain embodiments, the present invention relates to any one of the aforementioned methods, wherein the second piercable barrier comprises one or more polymers selected from the group consisting of polyacrylics, silicones, polyolefins, polystyrenes, polyesters, polyethers, polyurethanes, polycarbonates, polyamines, or co-polymers thereof.

In certain embodiments, the present invention relates to any one of the aforementioned methods, wherein the second piercable barrier comprises a metal.

In certain embodiments, the present invention relates to any one of the aforementioned methods, wherein the exterior surface of the second piercable barrier is paper coated with wax or plastic.

In certain embodiments, the present invention relates to any one of the aforementioned methods, further comprising a means of vibrating the housing.

In certain embodiments, the present invention relates to any one of the aforementioned methods, wherein the means of vibrating the housing is a piezoelectric vibrator.

In certain embodiments, the present invention relates to any one of the aforementioned methods, wherein the means of vibrating the housing is an electric motor vibrator.

In certain embodiments, the present invention relates to any one of the aforementioned methods, wherein the housing further comprises a third barrel.

In certain embodiments, the present invention relates to any one of the aforementioned methods, wherein the third barrel further comprises a third plunger, a third floating plunger, a third fluid bypass, and a third pressure valve between the distal end of the third barrel and the third floating plunger.

In certain embodiments, the present invention relates to any one of the aforementioned methods, wherein the third plunger comprises rubber. In certain embodiments, the present invention relates to any one of the aforementioned methods, wherein the third plunger comprises bromobutyl rubber. In certain embodiments, the third plunger further comprises a coating of lubricant. In certain embodiments, the lubricant is a medical grade silicone lubricant.

In certain embodiments, the present invention relates to any one of the aforementioned methods, wherein the third barrel further comprises a third plunger, a third floating plunger, a third fluid bypass, and a third hydrophobic filter at or near the distal end of the third barrel.

In certain embodiments, the present invention relates to any one of the aforementioned methods, wherein the third barrel further comprises a third floating plunger, a third fluid bypass, and a third check valve at or near the distal end of the third barrel. In certain embodiments, the present invention relates to any one of the aforementioned methods, wherein the third check valve is a rubber dome valve or bi-directional valve.

In certain embodiments, the present invention relates to any one of the aforementioned methods, further comprising an indicator light.

In certain embodiments, the present invention relates to any one of the aforementioned methods, wherein the applicator further comprises an indicator light, wherein the indicator light is a light emitting diode.

In certain embodiments, the present invention relates to any one of the aforementioned methods, wherein the first plunger and the second plunger are mechanically locked such that their ability to advance through the first barrel and the second barrel, respectively, is constrained to be substantially in unison.

In certain embodiments, the present invention relates to any one of the aforementioned methods, wherein the length of the first barrel is between about 0.5 inches to about 9 inches; or about 1.5 inches to about 4 inches; or about 2 inches to about 3 inches.

In certain embodiments, the present invention relates to any one of the aforementioned methods, wherein the diameter of the first barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the length of the second barrel is between about 0.5 inches to about 9 inches; or about 1.5 inches to about 4 inches; or about 2 inches to about 3 inches.

In certain embodiments, the present invention relates to any one of the aforementioned methods, wherein the diameter of the second barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the distal end of the second internal chamber has a first opening which has a diameter between about 0.1 inches and about 1 inch; or about 0.15 inches to about 0.38 inches; or about 0.2 inches to about 0.3 inches; or about 0.05 inches and about 0.5 inches; or about 0.08 inches to about 0.19 inches; or about 0.1 inches to about 0.15 inches; or about 0.01 inches and about 0.1 inch; or about 0.02 inches to about 0.04 inches.

In certain embodiments, the present invention relates to any one of the aforementioned methods, wherein the distal end of the fourth internal chamber has a second opening which has a diameter between about 0.1 inches and about 1 inch; or about 0.15 inches to about 0.38 inches; or about 0.2 inches to about 0.3 inches; or about 0.05 inches and about 0.5 inches; or about 0.08 inches to about 0.19 inches; or about 0.1 inches to about 0.15 inches; or about 0.01 inches and about 0.1 inch; or about 0.02 inches to about 0.04 inches.

In certain embodiments, the present invention relates to any one of the aforementioned methods, wherein the length of the nozzle assembly is between about 0.5 inches and about 15 inches; or about 0.75 inches to about 6 inches; or about 1 inch to about 2 inches.

In certain embodiments, the present invention relates to any one of the aforementioned methods, wherein the diameter of the outlet is between about 0.001 inches and about 1 inch; or about 0.01 inches to about 0.05 inches; or about 0.01 inches to about 0.04 inches; or about 0.01 inches to about 0.03 inches; or about 0.01 inches to about 0.02 inches.

In certain embodiments, the present invention relates to any one of the aforementioned methods, wherein instead of a fluid bypass, the floating plunger head contains a check valve which, when opened, connects the chambers in a given barrel.

In certain embodiments, the present invention relates to any one of the aforementioned methods, wherein instead of a floating plunger and bypass, a hydrophobic septum is used.

Sterilization Procedures

A variety of procedures can be used to sterilize the applicators and/or the chemical composition contained therein. Sterilization may be accomplished by, for example, chemical, physical, or irradiation techniques. In certain embodiments, a two part sterilization procedure can be used, comprising first using physical or irradiation sterilization techniques, and then using chemical sterilization techniques. In certain embodiments, a two-part sterilization procedure can be used when components in an applicator of the invention, such as circuitry, are not stable under certain sterilization conditions. For example, in certain embodiments, the housing comprising solids, viscous liquids and/or liquids can be sterilized using physical or irradiation sterilization techniques, and the housing has been incorporated into an applicator, the applicator can be sterilized by chemical sterilization techniques. Examples of such two part sterilizations are described in the Exemplification contained herein.

Examples of chemical methods include exposure to ethylene oxide or hydrogen peroxide vapor.

Examples of physical methods include sterilization by heat (dry or moist), retort canning, and filtration. The British Pharmacopoeia recommends heating at a minimum of 160° C. for not less than 2 hours, a minimum of 170° C. for not less than 1 hour and a minimum of 180° C. for not less than 30 minutes for effective sterilization. For examples of heat sterilization, see U.S. Pat. No. 6,136,326, which is hereby incorporated by reference.

Passing the chemical composition through a membrane can be used to sterilize a composition. For example, the composition is filtered through a small pore filter such as a 0.22 micron filter which comprises material inert to the composition being filtered. In certain instances, the filtration is conducted in a Class 100,000 or better clean room.

Examples of irradiation methods include gamma irradiation, electron beam irradiation, microwave irradiation, and irradiation using visible light. One method is electron beam irradiation, as described in U.S. Pat. Nos. 6,743,858; 6,248,800; and 6,143,805, each of which is hereby incorporated by reference. There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "canned" beam, prior to leaving the vacuum enclosure through a beam window. The dose can be adjusted with the control of the percent scan, the beam current, and the conveyor speed. In certain instances, the electron-beam radiation employed may be maintained at an initial fluence of at least about 2 µCurie/cm$^2$, at least about 5 µCurie/cm$^2$, at least about 8 µCurie/cm$^2$, or at least about 10 µCurie/cm$^2$. In certain instances, the electron-beam radiation employed has an initial fluence of from about 2 to about 25 µCurie/cm$^2$. In certain instances, the electron-beam dosage is from about 5 to 50 kGray, or from about 15 to about 20 kGray with the specific dosage being selected relative to the density of material being subjected to electron-beam radiation as well as the amount of bioburden estimated to be therein. Such factors are well within the skill of the art.

The applicators and/or composition to be sterilized may be in any type of at least partially electron beam permeable container such as glass or plastic. In embodiments of the present invention, the container may be sealed or have an opening. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

Procedures for sterilization using visible light are described in U.S. Pat. No. 6,579,916, which is hereby incorporated by reference. The visible light for sterilization can be generated using any conventional generator of sufficient power and breadth of wavelength to effect sterilization. Generators are commercially available under the tradename PureBright® in-line sterilization systems from PurePulse Technologies, Inc. 4241 Ponderosa Ave, San Diego, Calif. 92123, USA. The PureBright® in-line sterilization system employs visible light to sterilize clear liquids at an intensity approximately 90,000 times greater than surface sunlight. If the amount of UV light penetration is of concern, conventional UV absorbing materials can be used to filter out the UV light.

In one embodiment, the composition in the applicator is sterilized to provide an applicator with a Sterility Assurance Level (SAL) of at least about $10^{-3}$. The Sterility Assurance Level measurement standard is described, for example, in ISO/CD 14937, the entire disclosure of which is incorporated herein by reference. In certain embodiments, the Sterility Assurance Level may be at least about $10^{-4}$, at least about $10^{-5}$, or at least about $10^{-6}$.

As discussed above, in certain embodiments of the present invention, one or more of the compositions, reagents, or components of a kit has been sterilized. The sterilization may be achieved using gamma radiation, e-beam radiation, dry heat sterilization, ethylene oxide sterilization, or a combination of any of them. The compositions, reagents, or components of the kits can be sterilized in an aqueous solution or neat.

In certain embodiments a compound present in an applicator (as described herein) has been sterilized by e-beam radiation between 2-40 kGy; or between 3-20 kGy; or between 5-12 kGy. In certain embodiments, said sterilization is carried out below 30° C. In certain embodiments, said sterilization is carried out below 20° C. In certain embodiments, said sterilization is carried out below 10° C. In certain embodiments, said sterilization is carried out below 0° C.

Kits

In another aspect of the invention kits are provided containing one or more applicators of the invention. A "kit," as used herein, typically defines a package or an assembly including one or more of the applicators of the invention, and/or other compositions associated with the invention, for example, as described herein. In addition, in certain embodiments, such kits may include associated devices used to perform medical procedures. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, fits, filters, rings, clamps, wraps, patches, containers, and the like, for example, for using, modifying, assembling, storing, packaging, preparing, mixing, diluting, and/or preserving the compositions components for a particular use. In certain embodiments, different parts of the applicators may be packaged separately (e.g., in Mylar® pouches).

A kit of the invention may include instructions in any form that are provided in connection with the applicators of the invention in such a manner that one of ordinary skill in the art would recognize that the instructions are to be associated with the compositions of the invention. For instance, the instructions may relate to the use, modification, mixing, diluting, preserving, assembly, storage, packaging, and/or preparation of the applicators and/or other compositions associated with the kit. In some cases, the instructions may also include instructions for the use of the applicators. The instructions may be provided in any form recognizable by a user as a suitable vehicle for containing such instructions; for example, written or published, verbal, audible (e.g., telephonic), digital, optical, visual (e.g., videotape, DVD, etc.) or electronic communications (including Internet or web-based communications), provided in any manner.

In certain embodiments, a thermoformed tray or blister is used to retain and protect the applicator and its sterile barrier packaging. For example, a thin gage thermoplastic can be used to form a cavity into which the applicator can fit. In certain embodiments, some type of mechanical interference may be used so that the applicator is captured by the tray. In certain embodiments, the tray can be placed in a sterile barrier, such as a foil Mylar pouch or a Tyvek/Mylar pouch.

DEFINITIONS

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "nozzle" as used herein is known to those skilled in the art and refers to a mechanical device designed to control the characteristics of a fluid flow as it exits from an enclosed chamber (such as an applicator body) into some medium. A nozzle is often a tube of varying diameter, and it can be used to direct or modify the flow of a liquid or gas. Nozzles are frequently used to control the rate of flow, speed, direction, and/or the pressure of the stream that emerges from them. In certain embodiments the proximal end of a nozzle, wherein the fluid flow enters, will have a larger diameter than the distal end of a nozzle, where the fluid flow exists. This is known as a convergent nozzle (i.e., narrowing down from a wide diameter to a smaller diameter in the direction of the flow). In other embodiments the nozzle can be characterized as divergent (i.e., expanding from a smaller diameter to a larger one).

A trocar is a hollow cylinder with a sharply pointed end, often three-sided, that is used to introduce cannulas and other similar implements into blood vessels or body cavities. Trocars are also used as ports in laparoscopic surgery. A trocar is often passed inside a cannula, and functions as a portal for the subsequent placement of other devices, such as a chest drain or intravenous cannula. In certain embodiments described herein, the nozzle of the apparatus is designed to pass through a trocar port or equivalent on a endoscope or laproscope.

The term "brush" or "brush cannula" as used herein is known to those skilled in the art. The name represents the function of the brush: It is constructed to enable liquid to flow through the bristles for an application. The brushes can be attached to a wide variety of media that dispense liquid, and can be made out of many types of bristle material and configurations. In certain embodiments herein the brush cannula is connected to an applicator body. Brush cannulas are also known as flow-thru brushes; the terms are used interchangeably herein.

The term "activated PEG" as used herein is known to those skilled in the art and refers to poly(ethylene)glycols (both linear and branched) which have either at least one end activated for conjugation with other molecules. Shown below are chemical structures for polyethylene glycol (PEG), monomethylated polyethylene glycol (mPEG), an activated mPEG and a bis-activated PEG.

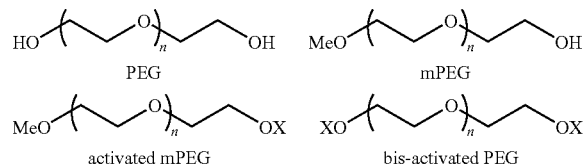

PEG    mPEG activated mPEG    bis-activated PEG

In the structures provided above n is a positive integer. In a batch of activated PEG different individual molecules will have a different values of n (i.e., the mixture is polydisperse); these mixtures are often characterized by an average molecular weight, which can be converted into an average value for n. In certain embodiments herein, the average n is between about 10 and about 200. In other embodiments the average n is between about 80 and about 120. In yet other embodiments, the average n is about 100. In the structures provided above, X can comprise a variety of chemical moieties such as, for example, a N-succinimide, a N-maleimide, a nitro, an aldehyde, an amine, a thiol, a ketal, an acetal, or a carbonate. In certain embodiments, X is selected from the group consisting of —$CH_2C(=O)O$(N-succinimidyl), —$(CH_2)_2C(=O)O$(N-succinimidyl), —$(CH_2)_3C(=O)O$(N-succinimidyl) ["PEG-SPA"], —$(CH_2)_4C(=O)O$(N-succinimidyl), —$(CH_2)_5C(=O)O$(N-succinimidyl), —$(CH_2)_6C(=O)O$(N-succinimidyl), —$(CH_2)_7C(=O)O$(N-succinimidyl), —$(CH_2)_8C(=O)O$(N-succinimidyl), —$(CH_2)_9C(=O)O$(N-succinimidyl), —$C(=O)CH_2C(=O)O$(N-succinimidyl), —$C(=O)(CH_2)_2C(=O)O$(N-succinimidyl), —$C(=O)(CH_2)_3C(=O)O$(N-succinimidyl) ["PEG-SG"], —$C(=O)(CH_2)_4C(=O)O$(N-succinimidyl) ["PEG-adipate"], —$C(=O)(CH_2)_5C(=O)O$(N-succinimidyl), —$C(=O)(CH_2)_6C(=O)O$(N-succinimidyl), —$C(=O)(CH_2)_7C(=O)O$(N-succinimidyl), —$C(=O)(CH_2)_8C(=O)O$(N-succinimidyl) ["PEG-sebacate"], —$C(=O)(CH_2)_9C(=O)O$(N-succinimidyl), —$C(=O)$(p-nitrophenyl), —$CH_2CH_2C(=O)H$, —$CH_2CH_2CH_2NH_2$, —$CH_2CH_2CH(OCH_2CH_3)_2$, —$CH_2CH_2SH$, —$CH_2CH_2CH_2N(H)C(=O)CH_2CH_2$(N-maleimidyl), and —$O(C=O)O$(p-nitrophenyl).

The term "PEG(NHS)$_2$" refers to a linear polyethylene glycol having —$C(=O)O$((N-succinimidyl) at both ends of the polymer chain. PEG(NHS)$_2$ can be prepared in variety of ways, such as by using either of the following methods. In method 1, a polyethylene glycol is subjected to oxidative conditions in order to oxidize the two termini to the corresponding carboxylic acids [$HO_2CCH_2O$-PEG-$OCH_2CO_2H$], followed by transformation to the bis(NHS ester). In method 2, PEG(NHS)$_2$ is prepared by alkylation of the two termini of a polyethylene glycol with acrylonitrile to give $NCCH_2CH_2O$-PEG-$OCH_2CH_2CN$, followed by hydrolysis to the bis(acid) [$HO_2CCH_2CH_2O$-PEG-$OCH_2CH_2CO_2H$], and then transformation to the bis(NHS ester).

As used here, "PEG-SPA" refers to the following structure:

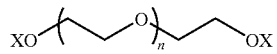

wherein X is —$(CH_2)_3C(=O)O$(N-succinimidyl); and n is an integer (e.g., from 10 to 200).

As used herein, "PEG-SG" refers to the following structure:

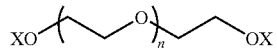

wherein X is —$C(=O)(CH_2)_3C(=O)O$(N-succinimidyl); and n is an integer (e.g., from 10 to 200).

As used herein, "PEG-adipate" refers to the following structure:

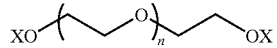

wherein X is —$C(=O)(CH_2)_4C(=O)O$(N-succinimidyl); and n is an integer (e.g., from 10 to 200).

As used herein, "PEG-sebacate" refers to the following structure:

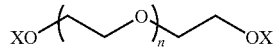

wherein X is —$C(=O)(CH_2)_8C(=O)O$(N-succinimidyl); and n is an integer (e.g., from 10 to 200).

As used herein, "plastic" refers to polyacrylics, silicones, polyolefins, polystyrenes, polyesters, polyethers, polyurethanes, polycarbonates, polyamines, or co-polymers thereof.

As used herein, "silicones" (polymerized siloxanes or polysiloxanes) are mixed inorganic-organic polymers with the chemical formula [$R_2SiO$]$_n$, where R may be an organic group such as methyl, ethyl, and phenyl. These materials consist of an inorganic silicon-oxygen backbone with organic side groups attached to the silicon atoms, which are four-coordinate. In some cases organic side groups can be used to link two or more of these backbones together. By varying the —Si—O— chain lengths, side groups, and crosslinking, silicones can be synthesized with a wide variety of properties and compositions.

As used herein, the term "patient" refers to any animal in need, including primates, in particular humans, and other mammals such as equines, cattle, swine and sheep; and poultry and pets in general.

The term "check valve" as used herein refers to a mechanical device, a valve, which normally allows fluid to flow through it in only one direction.

As used herein, the term "septum" refers to a partition separating two cavities or spaces, wherein the partition is permeable to liquids under certain conditions (such as in increase in pressure). A hydrophobic membrane is an example of a septum, as the term is used herein.

The term "fluid bypass" as used herein refers to a structural aspect of, for example, a syringe body, that allows fluid to flow from one compartment to another once a plunger head, or the like, is distally advanced. See, for example, U.S. Pat. No. 4,735,616, hereby incorporated by reference, which describes a twin bypass syringe for the delivery of fibrin glue products As used herein, the term "discrete logic" refers to a hardware circuit that computes one or more logic functions without using software. Specifically, the circuit is comprised of various types of logic gates which turn one or more dynamic inputs into single outputs based on the arrangement of the gates.

EXEMPLIFICATION

The invention now being generally described, it will be more readily understood by reference to the following examples which are included merely for purposes of illustration of certain aspects and embodiments of the present invention, and are not intended to limit the invention.

Example 1

FIG. 1 shows one embodiment of the invention. The device shown in FIG. 1 utilizes two syringe-like cylindrical chambers (1) that house the four components of a hydrogel forming activated PEG formulation. Details of these chambers will be described more fully below. The applicator also has a nozzle assembly (2) which incorporates three channels of fluid flow. Two channels are connected directly to the distal ends of the two cylindrical syringe-like material chambers and a third channel is connected to a small electrical air pump (5). A small electric motor (3) drives the syringe plungers forward through the use of a gear train (4). A small integrated circuit (6) with a programmable logic controller (PLC) is used to regulate the many functions of the applicator gun. A sliding trigger (7) engages a contact switch thus signaling to the PLC when the trigger has been activated. The device is powered by two AA size batteries (8) housed within the housing. A lock out button (9) prevents the plungers from moving forward beyond the reconstitution phase unless the button is pushed.

Figure 2:
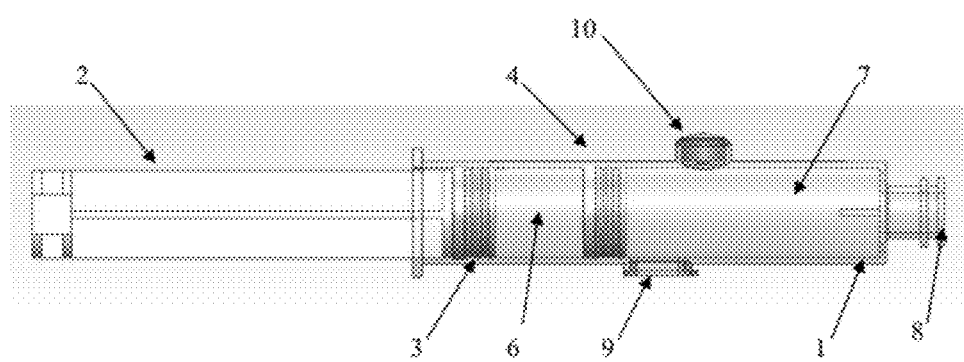
FIG. 2 depicts [A] a side view and [B] a top view of one embodiment of a device with cylindrical syringe-like material chambers and plungers.
Figure 2:
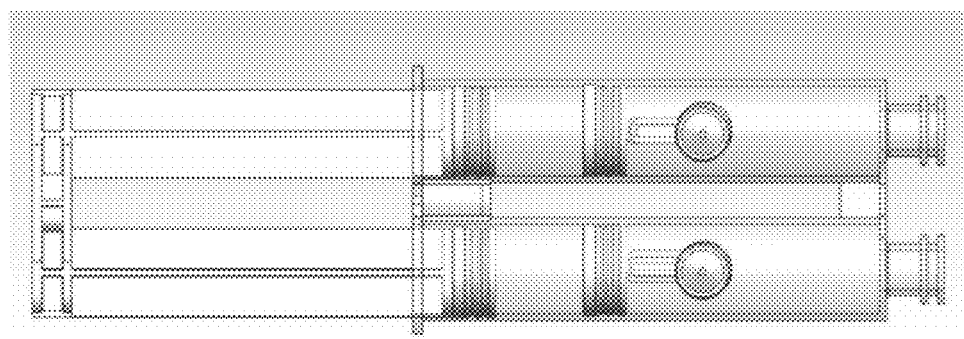

A detailed picture of the cylindrical syringe-like material chambers and plungers can be seen in FIG. 2. This is the "engine" for the applicator gun. Each of the cylindrical syringe-like material reservoirs (11) is separated into two chambers by the floating plunger (14). The front chamber is sealed on the distal end by a foil seal (not shown) which is adhered to the front face (18) of the distal discharge end of the syringe-like chamber. The floating plunger (14) constitutes the proximal end of the front chamber. The front chambers will house the PEG and PEI separately in the two sides of the device. The back chamber (16) is sealed on the distal end by the floating plunger (14) and on the proximal end by the driven plunger (13). The push rod (12) is mechanically connected to the electric drive train and provides the forward thrust which ultimately reconstitutes the PEG and PEI and then expels these components into the nozzle assembly. In addition to the above described features, there is also a bypass (19) purposely built into the cylindrical chamber and a pressure bleed off vent (20) which will be described further below.

Example 2

One method of use for the applicator describer in FIG. 1 is outlined below. As mentioned above, during manufacture the PEG and the PEI will be separately deposited in the front chambers of the cylindrical vessels. The two buffer solutions are deposited in the back chambers and the distal end of the back chamber is sealed with the driven rubber plungers. At time of use, the device will go through a reconstitution step and then an application step. During the reconstitution step, the pushrod is advanced forward which causes the driven plunger to be pushed forward. The driven plunger therefore exerts a force on the liquid contained within the rear chambers, pressurizing it. The pressurized liquid columns then exert a force on the proximal surface of the floating plunger causing it to move forward (or distally). This continues until the floating plunger advances to the bypass at which time the liquid previous contained within the rear chamber can bypass the floating plunger and thus flows into the front chambers. The pushrod is advanced until such time as the driven plunger approximately contacts the floating plunger and thus all of the fluid that was formerly in the rear chambers is now conveyed to the front chambers. During this reconstitution phase, the pressure bleed off valves automatically open to vent the front chambers and prevent them from pressurizing. This constitutes the end of the reconstitution phase. Once the reconstitution of the PEI and the PEG have been accomplished, further forward movement of the push rod causes the driven and floating plungers to move forward. The plungers now block the bypass and liquid is expelled through the front of the cylindrical chambers.

Example 3

One approach to the assembly and use of an applicator is provided below. The "engine" (one embodiment described above in Example 1) would be loaded with PEI, PEG and two buffer solutions. The loaded "engine" would then be placed within the housing and the other components (air pump, tubing, printed circuit board, drive mechanism, electric motor, nozzle and lock-out assembly, etc.) will be assembled. The assembled device will be packaged, sterilized and shipped to a physician/user. At time of use, the device will be removed from its packaging and placed into the sterile field of an operating room (OR). The OR staff will energize the device by either pulling a pull tab engaging the batteries or manually inserting batteries into the device. A physician or scrub nurse will then pick up the device and push the trigger. This will send an electrical signal to the PLC telling it to start the reconstitution phase. The motor will energize, pushing the pushrod forward and going through the steps outlined above for reconstitution. The PLC will then stop any forward advance of the push rod until a preset time is reached. Further pushing of the trigger does nothing until the preset time has been reached. At this time an optional yellow LED light can be energized by the PLC signifying to the user that the gun is still in the middle of the reconstitution phase. After the preset time has expired, a green LED indicator light is energized by the PLC signifying to the user that the device is ready for use. (The preset time is chosen such that the PEI and PEG materials will have ample time to dissolve in their buffers.) Once the green light is energized, the user will push the lockout button which releases the back end of the cylindrical chambers, signals to the PLC that the gun is ready for formulation delivery and the air pump is turned on. The next trigger pull will send an electrical signal to the PLC telling it to start the motor and drive train. This will push the cylindrical chambers forward (distally) and cause the foil seals to be pierced by pierces inside the nozzle assembly. As long as the trigger is pulled, the PLC will continue to advance the motor which will force the push rod forward, expelling the two liquid streams into the nozzle. Remembering that the air pump has already been turned on, the two liquid streams and the air mix within the nozzle assembly and exit out the most distal end of the nozzle assembly as a fully mixed stream with enough speed to be propelled to the surface to be treated. If the trigger is allowed to return to its non-depressed position, the PLC will no longer receive an electric signal from the trigger assembly and will stop the forward motion of the drive train. The air pump will stay on. In an embodiment, the air would be turned off after an extended time without further trigger pulls (for example greater than about 5 minutes) in order to save battery power. A second trigger pull will start the drive train again and the device will begin to expel aerosolized formulation again. This on-off cycle can continue as many times as is desired by the physician or until the formulation is completely expelled. The device is engineered such that after all of the formulation has been deployed, the plungers will meet the end of their travel within the cylindrical chambers and will make contact with the chamber wall. This will cause the motor to attempt to push harder and thus will increase the power (and thus amperage) of the electrical service to the motor. A properly sized fuse will detect this increase in amperage and will de-energize the device so that no further actions can be accomplished and for all intents and purposes, the device is ready for placement in the waste stream.

Example 4

An applicator of FIG. 1 was loaded with PEG-SSebacate and PEI in the front chambers and with appropriate buffer solutions in the back chambers. The applicator device was then assembled and the trigger was pulled to begin the reconstitution phase. After five minutes has elapsed, the trigger was again pulled and burst strength specimens were produced. The burst strength specimen uses a standardized collagen sausage casing which has a 3 mm through hole placed in the center. A spray application of the polymerizing hydrogel formulation was made covering the 3 mm diameter through hole to a depth of approximately 2 mm and was allowed to completely gel. The specimen was then placed into the test fixture which slowly applied pressurized water to the lower surface of the collagen sheet. The pressure to disrupt the hydrogel repair was thus measured. The hydrogel repair was found to have an average burst strength of 333.4 cm of water with a standard deviation of 55.8 cm of water (n=3). It is generally accepted that intracranial pressure during val salva maneuver can be as high as approximately 50 cm of water.

Example 5

An applicator of FIG. 1 fitted with a staggered nozzle (see FIG. 6) was loaded with PEG-SSebacate, PEI and appropriate buffer solutions as described in Example 4. It was likewise used to make burst strength samples as described in Example 4. The hydrogel repair was found to have an average burst strength of 321.7 cm of water with a standard deviation of 19.5 cm of water (n=3).

Example 6

It has been found that electronic circuitry is difficult to sterilize via normal radiation sterilization procedures. To address this problem, a hybrid sterilization system was used in which a sealed, filled mixing chamber with two active ingredients and two buffer solutions was first sterilized via radiation then assembled into a gun comprising, which was then sterilized via ethylene oxide gas. Hydrogen peroxide could also be used.

Example 7

Another strategy for producing a sterilized applicator of the invention is to utilize only simple analog circuitry to drive the device. This strategy allows the applicator to be sterilized via traditional radiation sterilization methods since the simple analog circuitry is not effected by radiation. One type of analog circuitry which may be used is shown in FIG. 7 (top). In this embodiment, a motor and an air pump are controlled by a few switches. In use, the user would pull and hold the trigger. This would complete the power circuit to the drive motor and effect reconstitution. The drive motor would continue to move forward until the normally closed switch is opened. The opening of this switch would occur at end of the reconstitution step. At the same time, the normally open switch closes (these may in fact be a single double position switch, see FIG. 7 (bottom)). The original power circuit to the motor thus opens stopping the motor. At this point, pulling the trigger does nothing. After a time, as instructed, the user would push the button on the top of the gun, closing two switches. One of those switches closes the power circuit to the air pump and it turns on. The second switch arms the drive motor power circuit. Pulling the trigger now completes the power circuit to the drive motor allowing the reconstituted active ingredients to be delivered into the air stream and sprayed out of the nozzle of the gun applicator.

Example 8

Figure 8:
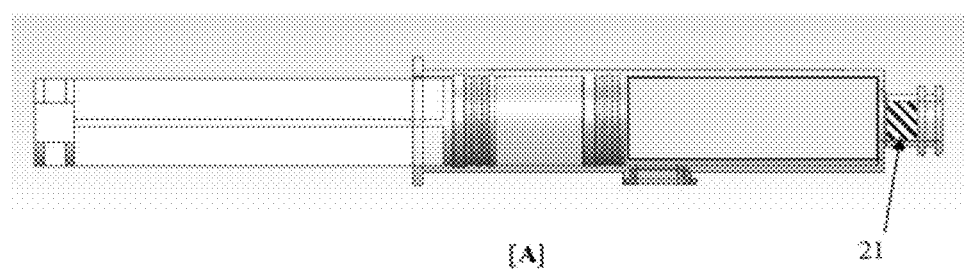
FIG. 8 depicts [A] a side view and [B] a top view of one embodiment of a double barrel applicator with hydrophobic filters at the distal ends of the barrels.
Figure 8:
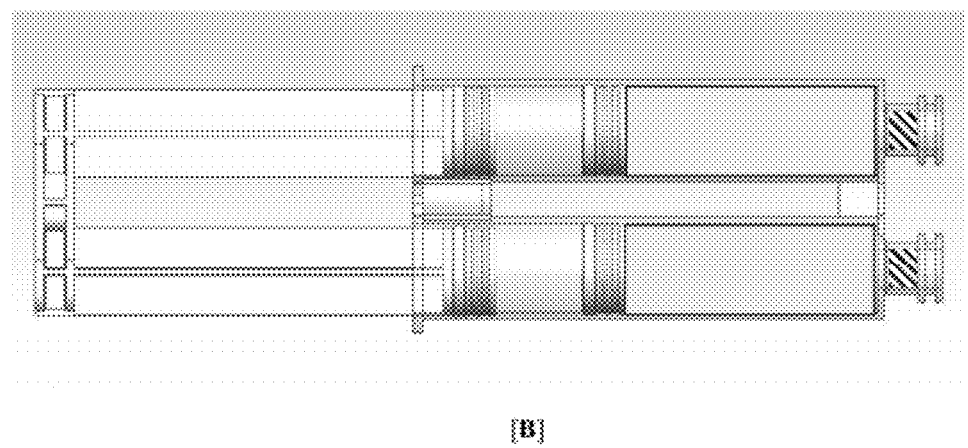
Figure 9:
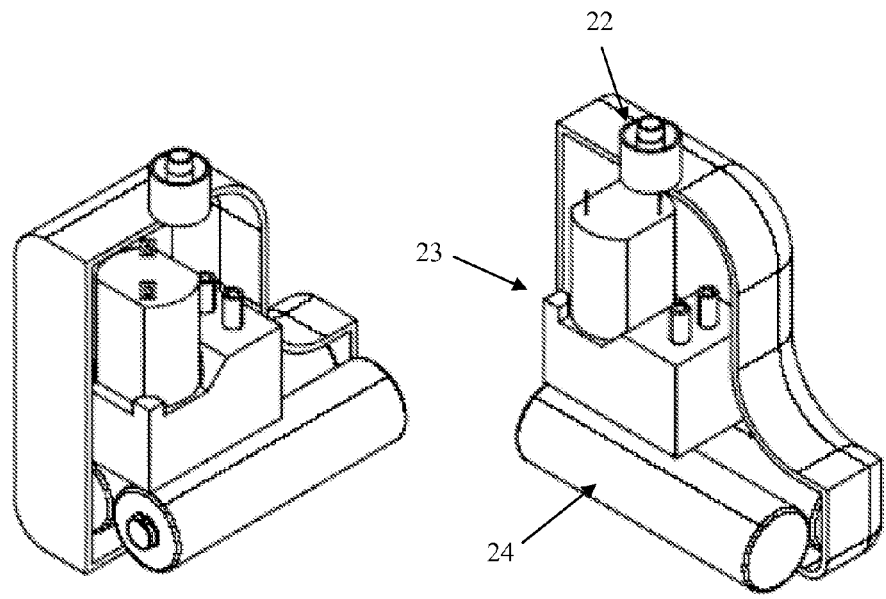
FIG. 9 depicts several views of an air pump housing containing an air pump, a luer lock adapter on the discharge end of the air pump, and batteries.
Figure 9:
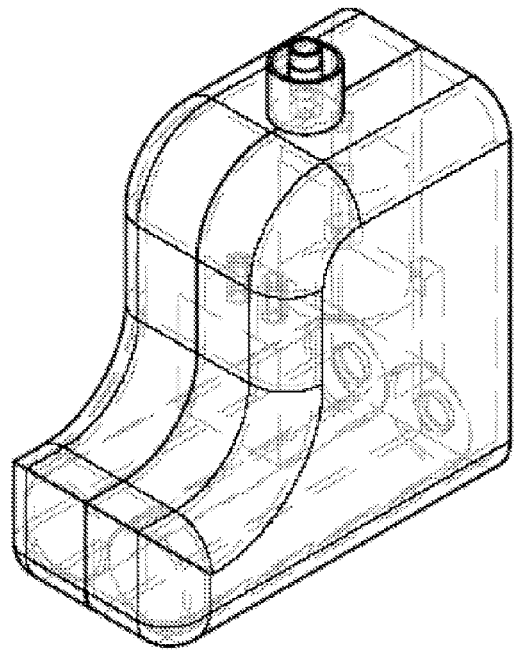
Figure 10:
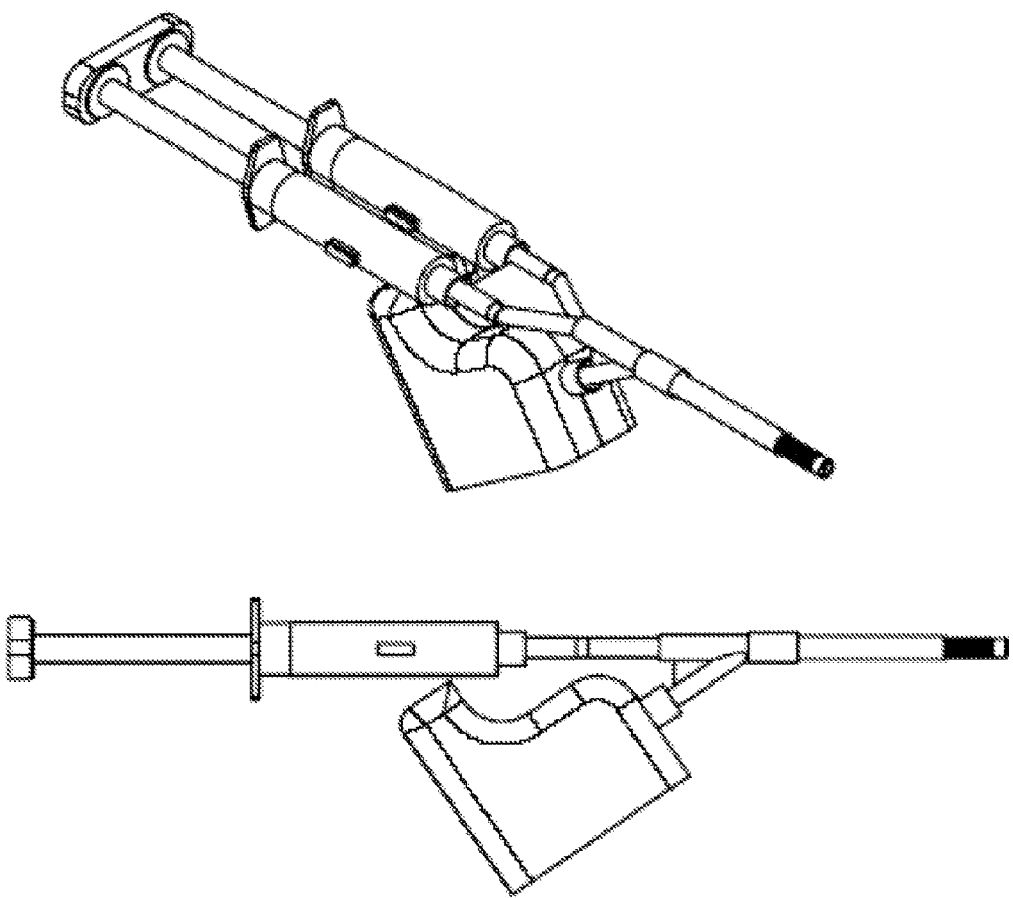
FIG. 10 depicts the air pump housing of FIG. 9 attached to one embodiment of an applicator.

FIG. 8 shows another embodiment of the invention. This embodiment incorporates a filled mixing chamber that will allow the device to undergo a first radiation sterilization process of the filled mixing chamber, an assembly process to assembly the sterilized filled mixing chambers into a gun applicator, and lastly, a second ethylene oxide sterilization procedure. In order for this strategy to be successful, the filled mixing chamber must be a sealed entity, for at least two reasons. The first reason is that in order for the internal parts of the filled mixing chamber to remain sterile during the assembly process, there can not be any communication between the inside aspects of the filled mixing chamber and the outside environment. The second reason is that the ethylene oxide gas may react with the chemical components in the mixing chamber, e.g., activated PEG or PEI.

In the embodiment of Example 1, the umbrella valves in the front portions of each of the sides of the filled mixing chamber allowed the excess pressure developed in the front chambers during the reconstitution phase to vent. However, under the conditions of the ethylene oxide sterilization cycle, the ethylene oxide gas easily went through the valve thus affecting the activity of the chemical components in the mixing chamber. It was therefore necessary to determine a new way to bleed air during the reconstitution stage without letting reconstituted active ingredients prematurely enter the nozzle area before the air pump is turned on.

In the embodiment shown in FIG. 8, the umbrella valve has been removed in favor of hydrophobic filters placed into the inside aspect of both sides of the filled mixing chamber near to the most distal exit of the mixing chamber (21). In certain embodiments, a foil seals sit on the exterior most distal exit ports of the filled mixing chamber. Thus, the filled mixing chamber is completely sealed, and can be radiation sterilized, placed into a gun applicator and subjected to the ethylene oxide sterilization process. At time of use, the user would push the gate button, unlocking the forward travel of the filled mixing chamber. The user would then pull the trigger with the gun pointed tip up which initiates a reconstitution phase. The drive motor would turn on, driving the mixing chamber forward, piercing both foil seals. The interior of the mixing chamber is now in fluid communication with the exit port of the nozzle. Continued forward motion of the motor will force the reconstitution liquids forward and the excess air pressure can be vented out the nozzle of the gun. Upon completion of the reconstitution phase, the user can place the gun on its side as normally done and the hydrophobic filters prevent leakage of the reactive reconstituted active ingredients into the nozzle where they could polymerize and clog the nozzle.

Example 9

Shown in FIG. 9 is an air pump hosing comprising a battery operated air pump (23) with an internal battery pack (24), an exterior on/off switch (not shown) and a luer lock fitting (22) at the discharge end of the pump. A user would reconstitute the active ingredients manually, then attach the reconstituted syringes into a nozzle assembly and then attach the battery powered air pump. The user would turn on the pump and supply manual pressure to advance the two reconstituted active ingredients into the air stream, thus producing an adhesive spray for application onto tissue.

As shown in FIG. 10, the air pump housing of FIG. 9 can be attached to an applicator comprising two bypassing syringes attached to the nozzle assembly. Reconstitution is accomplished by manually applying pressure to the back of the double plungers to advance the reconstitution liquids into the front of the syringes. A stop would prevent further advancement beyond the reconstitution phase. This stop or lockout feature would then be removed or disabled, and further advance will produce two liquid streams which mix with the air from the self-contained battery powered air pump, thus producing an adhesive spray for application onto tissue.

Example 10

Melt processing of activated PEG, along with some further mechanical processing of the resulting product, are described below.

1. Activated PEG was placed into a glass vial and heated to 80° C. for 30 minutes in order to fully melt the powder. The resulting liquid was placed into the syringe of a repeating pipetter and placed in 50 mL aliquots onto a dry lab bench. Once cooled, 1 gram of activated PEG beads were placed into a syringe and reconstituted. The activated PEG beads were dissolved within approximately 10 minutes and were found to be free from substantial amounts of air or foaminess.

2. Beads as described immediately above were subjected to an additional reduction in particle size by cutting with a razor blade. The resulting material was a coarse powder or somewhat varying particle size. One gram of the resulting material was placed into a syringe and reconstituted. The activated PEG particles were substantially dissolved within 5 minutes and were found to be free from substantial amounts of air or foaminess.

3. Activated PEG powder was placed into a glass vial and heated to 80° C. for 30 minutes in order to fully melt the powder. The resulting liquid was placed into a 3 cc syringe. The 3 cc syringe was placed onto an air assisted sprayer and hooked up to a source of compressed air. The melted PEG was then pressurized and thus introduced into the air stream of the sprayer. The resulting spray of molten PEG occurred approximately 5 feet above the surface of a clean lab bench. The resulting material was removed from the surface of the lab bench resulting in an extremely fine powder. This powder had a bulk density of approximately 0.5 g/cc. 1 gram of this powder was placed into a 5 cc syringe and reconstituted. The reconstituted PEG having a volume of approximately 3 mL was found to have a compressibility of approximately 0.2 cc due to dissolved or entrapped air. This was compared to a similar syringe of 1 gram of 0.25 g/cc bulk density powder formed by recrystallization which had compressibility of approximately 0.5 cc due to dissolved or entrapped air.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An applicator comprising a housing and a nozzle assembly; wherein (i) the housing comprises a first barrel, comprising a first diameter, a first end, and a second end;

a first internal chamber, comprising a proximal end and a distal end;

a second internal chamber, comprising a proximal end and a distal end;

a first floating plunger, located within the first barrel and under pressure movable therethrough, separating the first internal chamber from the second internal chamber, thereby forming the distal end of the first internal chamber, and the proximal end of the second internal chamber;

a first plunger, comprising a first end and a second end, the second end of the first plunger is located at least partially within the first end of the first barrel and under pressure movable therethrough, thereby forming the proximal end of the first internal chamber;

a first fluid bypass, located on the first barrel, external to the second internal chamber;

a first piercable barrier, located at the distal end of the second internal chamber;

a second barrel comprising a second diameter, a first end, and a second end;

a third internal chamber, comprising a proximal end and a distal end;

a fourth internal chamber, comprising a proximal end and a distal end;

a second floating plunger, located within the second barrel and under pressure movable therethrough, separating the third internal chamber from the fourth internal chamber, thereby forming the distal end of the third internal chamber, and the proximal end of the fourth internal chamber;

a second plunger, comprising a first end and a second end, the second end of the second plunger is located at least partially within the first end of the second barrel and under pressure movable therethrough, thereby forming the proximal end of the third internal chamber;

a second fluid bypass, located on the second barrel, external to the fourth internal chamber;

a second piercable barrier, located at the distal end of the fourth internal chamber;

(ii) the nozzle assembly comprises a first inlet and a first piercer, wherein the first piercer is suitably positioned to pierce the first piercable barrier, and thereby connect the first inlet to the second internal chamber; and the a second inlet and a second piercer, wherein the second piercer is suitably positioned to pierce the second piercable barrier, and thereby connect the second inlet to the fourth internal chamber;

a gas inlet; and an outlet in fluid communication with the first inlet, the second inlet and the gas inlet.

2. The applicator of claim 1, wherein the applicator further comprises a drive train and a locking mechanism;

the drive train comprises a motor and a gear train, wherein the motor is connected to the gear train; the gear train is attached to the first end of the first plunger; and the gear train is attached to the first end of the second plunger; and the lock mechanism is initially positioned to prevent the housing from substantially moving towards the nozzle assembly, thereby initially preventing the first piercer from piercing the first piercable barrier and initially preventing the second piercer from piercing the second piercable barrier.

3. The applicator of claim 2, further comprising a trigger; wherein activating the trigger starts the drive train, thereby compressing the first plunger and the second plunger and opening the first fluid bypass and the second fluid bypass.

4. The applicator of claim 1, wherein the applicator body further comprises a liquid in the first internal chamber; and the liquid is a buffer.

5. The applicator of claim 1, wherein the applicator body further comprises a liquid in the third internal chamber; and the liquid is a buffer.

6. The applicator of claim 1, wherein the applicator body further comprises a viscous liquid in the second internal chamber; and the viscous liquid comprises a polyalkyleneimine.

7. The applicator of claim 1, wherein the applicator body further comprises a solid in the fourth internal chamber; and the solid comprises an activated PEG.

8. The applicator of claim 1, wherein the housing further comprises a first pressure valve, located on the first barrel, external to the second internal chamber; and a second pressure valve, located on the second barrel, external to the fourth internal chamber.

9. The applicator of claim 1, wherein the housing further comprises a first hydrophobic filter, located at or near the distal end of the second internal chamber; and a second hydrophobic filter, located at or near the distal end of the fourth internal chamber.

10. The applicator of claim 1, wherein the housing further comprises a first check valve, located at or near the distal end of the second internal chamber; and a second check valve, located at or near the distal end of the fourth internal chamber.

11. The applicator of claim 1, wherein the nozzle is designed so that gas entering the gas inlet combines with material from the first inlet before the resulting mixture combines with material from the second inlet;

or wherein the nozzle is designed so that gas entering the gas inlet combines with material from the second inlet before the resulting mixture combines with material from the first inlet.

12. The applicator of claim 1, wherein the nozzle further comprises a brush, a sponge, a foam swab, a porous plastic component, a duck bill tip, a textile mitt or a spray tip affixed to the outlet.

13. The applicator of claim 1, wherein the nozzle further comprises a tubular fitment comprising two open ends; one end of the tubular fitment is affixed to the outlet; and the tubular fitment is adapted to pass through an endoscope or a laparoscope;

or the nozzle further comprises a tubular fitment comprising two open ends; one open end of the tubular fitment is affixed to the outlet and the other open end of the fitment has a flattened opening relative to the open end affixed to the outlet;

or the nozzle further comprises a tubular fitment comprising two open ends; one open end of the tubular fitment is affixed to the outlet and the other open end of the fitment comprises a protruding spatula-like piece.

14. The applicator of claim 1, further comprising an atomization fluid pathway; wherein said atomization fluid pathway is configured to expel any material in the nozzle out of the nozzle through the outlet.

15. The applicator of claim 1, further comprising an air pump.

16. The applicator of claim 15, wherein the air pump is contained within an air pump housing which further comprises batteries and an adapter at a discharge end of the air pump; and the discharge end of the air pump is in fluid communication with the gas inlet of the nozzle assembly.

17. The applicator of claim 1, further comprising a power source, wherein said power source is contained within the applicator.

18. The applicator of claim 1, further comprising a power source, wherein said power source is outside of the applicator.

19. The applicator of claim 1, wherein the distal end of the second internal chamber has a first opening which has a diameter between about 0.1 inches and about 1 inch; and the distal end of the fourth internal chamber has a second opening which has a diameter between about 0.1 inches and about 1 inch.

20. A method of using an applicator to apply a composition to a surface, wherein the applicator is an applicator of claim 1, wherein the housing further comprises a first liquid in the first internal chamber, a second liquid in the third internal chamber, a viscous liquid in the second internal chamber, and a solid in the fourth internal chamber;

comprising the steps of:

advancing the first plunger towards the second end of the first barrel, thereby advancing the first floating plunger towards the second end of the first barrel and over the first fluid bypass, and placing the first internal chamber in fluid communication with the second internal chamber;

advancing the second plunger towards the second end of the second barrel, thereby advancing the second floating plunger towards the second end of the second barrel and over the second fluid bypass, and placing the third internal chamber in fluid communication with the fourth internal chamber;

substantially advancing the housing toward the nozzle assembly, thereby piercing the first piercable barrier with the first piercer and the second piercable barrier with the second piercer, placing the second internal chamber in fluid communication with the nozzle, placing the fourth internal chamber in fluid communication with the nozzle, and forming a pre-composition mixture in the nozzle; and applying the pre-composition mixture to the surface, wherein the mixture gels to form the composition on the surface.

* * * * *